United States Patent
Jenison et al.

(10) Patent No.: US 9,981,124 B2
(45) Date of Patent: May 29, 2018

(54) DEVICES AND TECHNIQUES FOR DETECTING MAGNETIC RESONANCE IMAGING FIELD

(75) Inventors: Troy A. Jenison, Minneapolis, MN (US); Larry C. McClure, Forest Lake, MN (US); Christopher C. Stancer, Prescott, WI (US)

(73) Assignee: Medtronic, Inc., Minneapolis, MN (US)

( * ) Notice: Subject to any disclaimer, the term of this patent is extended or adjusted under 35 U.S.C. 154(b) by 1115 days.

(21) Appl. No.: 13/456,891

(22) Filed: Apr. 26, 2012

(65) Prior Publication Data

US 2013/0289384 A1    Oct. 31, 2013

(51) Int. Cl.
| | |
|---|---|
| A61N 1/08 | (2006.01) |
| A61N 1/39 | (2006.01) |
| A61N 1/36 | (2006.01) |
| A61N 1/37 | (2006.01) |
| A61N 1/372 | (2006.01) |
| G01R 33/28 | (2006.01) |

(52) U.S. Cl.
CPC .............. *A61N 1/08* (2013.01); *A61N 1/3718* (2013.01); *A61N 1/36142* (2013.01); *A61N 1/3706* (2013.01); *A61N 1/37211* (2013.01); *A61N 1/3956* (2013.01); *G01R 33/288* (2013.01)

(58) Field of Classification Search
CPC .... A61N 1/08; A61N 1/3718; A61N 1/36142; A61N 1/3706; A61N 1/3956; A61N 1/37211; G01R 33/288
USPC ........................................................ 600/411
See application file for complete search history.

(56) References Cited

U.S. PATENT DOCUMENTS

| 5,438,990 A | 8/1995 | Wahlstrand et al. |
| 5,545,187 A | 8/1996 | Bergstrom et al. |
| 5,629,622 A | 5/1997 | Scampini |
| (Continued) | | |

FOREIGN PATENT DOCUMENTS

| CN | 1762510 | 4/2006 |
| EP | 1 493 460 A1 | 6/2004 |
| (Continued) | | |

OTHER PUBLICATIONS

U.S. Appl. No. 13/046,158; Inventor: Troy Jenison, filed Mar. 11, 2011; 38 pages.

(Continued)

*Primary Examiner* — Amanda Lauritzen Moher
*Assistant Examiner* — Lisa Kinnard

(57) ABSTRACT

A device includes a housing configured to be implanted in a patient. The device also includes a first magnetic field direction sensor located at a first location within the housing and configured to generate a signal representative of a first direction of a magnetic field at the first location, a second magnetic field direction sensor located at a second location within the housing and configured to generate a signal representative of a second direction of the magnetic field at the second location, and a magnetic field strength sensor configured to generate a signal representative of a strength of the magnetic field. The device further includes a control module configured to identify a source of the magnetic field based on at least one of the signal representative of the strength of the magnetic field and the signals representative of the first and second directions of the magnetic field.

27 Claims, 8 Drawing Sheets

(56) References Cited

U.S. PATENT DOCUMENTS

| | | |
|---|---|---|
| 5,662,694 A | 9/1997 | Lidman et al. |
| 5,697,958 A | 12/1997 | Paul et al. |
| 5,709,225 A | 1/1998 | Budgifvars et al. |
| 5,722,998 A | 3/1998 | Prutchi et al. |
| 6,101,417 A | 8/2000 | Vogel et al. |
| 6,209,764 B1 | 4/2001 | Hartlaub et al. |
| 6,437,561 B1* | 8/2002 | Bartingale et al. ...... 324/207.22 |
| 6,510,345 B1 | 1/2003 | Van Bentem |
| 6,522,920 B2 | 2/2003 | Silvian et al. |
| 6,580,947 B1 | 6/2003 | Thompson |
| 6,839,596 B2 | 1/2005 | Nelson et al. |
| 6,937,906 B2 | 8/2005 | Terry et al. |
| 6,963,779 B1 | 8/2005 | Balakrishnan |
| 6,965,792 B2 | 11/2005 | Avrin et al. |
| 7,016,730 B2* | 3/2006 | Ternes .............................. 607/17 |
| 7,050,855 B2 | 5/2006 | Zeijlemaker et al. |
| 7,076,283 B2 | 7/2006 | Cho et al. |
| 7,174,202 B2* | 2/2007 | Bladen et al. ................. 600/424 |
| 7,231,251 B2 | 6/2007 | Yonce et al. |
| 7,239,134 B2 | 7/2007 | McClure et al. |
| 7,369,898 B1* | 5/2008 | Kroll ...................... A61B 5/055 |
| | | 600/411 |
| 7,509,167 B2 | 3/2009 | Stressman |
| 7,561,915 B1* | 7/2009 | Cooke et al. ................... 607/31 |
| 7,639,006 B2 | 12/2009 | Deffeyes |
| 7,672,726 B2 | 3/2010 | Ginggen |
| 8,014,856 B2 | 9/2011 | Wedan |
| 8,121,678 B2 | 2/2012 | Linder et al. |
| 8,200,334 B1* | 6/2012 | Min ...................... A61N 1/3718 |
| | | 607/27 |
| 8,768,486 B2* | 7/2014 | Gray ........................ A61N 1/37 |
| | | 607/115 |
| 8,805,496 B2 | 8/2014 | Ellingson |
| 2003/0144704 A1 | 7/2003 | Terry et al. |
| 2004/0088012 A1* | 5/2004 | Kroll .................... A61N 1/3718 |
| | | 607/9 |
| 2006/0173295 A1 | 8/2006 | Zeijlemaker |
| 2006/0276850 A1 | 12/2006 | Deffeyes |
| 2007/0173890 A1 | 7/2007 | Armstrong |
| 2007/0173910 A1 | 7/2007 | Armstrong |
| 2008/0154342 A1* | 6/2008 | Digby .................. A61N 1/3718 |
| | | 607/63 |
| 2008/0154346 A1 | 6/2008 | Smith et al. |
| 2008/0221638 A1 | 9/2008 | Wedan et al. |
| 2008/0228092 A1 | 9/2008 | Wedan |
| 2009/0096413 A1* | 4/2009 | Partovi et al. ................. 320/108 |
| 2009/0138058 A1 | 5/2009 | Cooke et al. |
| 2009/0157146 A1 | 6/2009 | Linder et al. |
| 2009/0204182 A1* | 8/2009 | Ameri .............................. 607/63 |
| 2009/0210025 A1 | 8/2009 | Ameri |
| 2009/0237073 A1* | 9/2009 | Uchiyama et al. ....... 324/207.11 |
| 2010/0106227 A1 | 4/2010 | Min et al. |
| 2010/0137946 A1 | 6/2010 | Gadagkar et al. |
| 2010/0152805 A1 | 6/2010 | Zeijlemaker |
| 2010/0176808 A1 | 7/2010 | Legay |
| 2010/0211123 A1 | 8/2010 | Stubbs et al. |
| 2010/0292759 A1 | 11/2010 | Hahn et al. |
| 2011/0148365 A1 | 6/2011 | Doerr |
| 2011/0148400 A1 | 6/2011 | Doerr et al. |
| 2011/0152667 A1 | 6/2011 | Doerr et al. |
| 2011/0160565 A1 | 6/2011 | Stubbs et al. |
| 2011/0160786 A1 | 6/2011 | Stubbs et al. |
| 2011/0202104 A1* | 8/2011 | Butala ............................. 607/30 |
| 2012/0053652 A1* | 3/2012 | Dianaty .................. A61N 1/08 |
| | | 607/30 |
| 2012/0105059 A1* | 5/2012 | Doerr et al. ................. 324/307 |

FOREIGN PATENT DOCUMENTS

| | | |
|---|---|---|
| EP | 1 935 450 A1 | 11/2007 |
| JP | H08-334570 | 12/1996 |
| JP | 2007-285865 | 11/2007 |
| WO | 02/103651 A1 | 12/2002 |
| WO | 2006/081434 A1 | 8/2006 |
| WO | 2006/124481 A2 | 11/2006 |
| WO | 2010/039877 A1 | 4/2010 |
| WO | 2010096138 A1 | 8/2010 |
| WO | 2010089866 A1 | 12/2010 |
| WO | WO 2011051955 A2 * | 5/2011 |
| WO | 2011/100241 A1 | 8/2011 |
| WO | 2012/102744 A1 | 8/2012 |

OTHER PUBLICATIONS (PCT/US2013/036867) PCT Notification of Transmittal of the International Search Report and the Written Opinion of the International Searching Authority, 12 pages.

Office Action from JP Patent Application No. 2013-551957, dated Apr. 9, 2015, 4 pages.

Office Action from CN Patent Application No. 201380022239.2, dated Aug. 31, 2015, 22 pages.

* cited by examiner

DEVICES AND TECHNIQUES FOR DETECTING MAGNETIC RESONANCE IMAGING FIELD

TECHNICAL FIELD

The disclosure relates to techniques for detecting magnetic resonance imaging (MRI) devices, and more particularly, to implantable medical devices capable of detecting MRI environments.

BACKGROUND

Magnetic resonance imaging (MRI) is a medical imaging technique used to visualize detailed internal structures of a patient. A patient is placed at least partially within an MRI device during an MRI scan. The MRI device may generate a variety of magnetic and electromagnetic fields, including a static magnetic field (hereinafter "static MRI field"), gradient magnetic fields, and radio frequency (RF) fields. The static MRI field may be generated by a primary magnet within the MRI device and may be present prior to initiation of the MRI scan. The gradient magnetic fields may be generated by electromagnets and may be present during the MRI scan. The RF magnetic fields may be generated by transmitting/receiving coils and may be present during the MRI scan. If the patient undergoing the MRI scan has an implantable medical device (IMD), the various fields produced by the MRI device may interfere with the operation of the IMD.

SUMMARY

To reduce the effects that the various fields produced during an MRI scan have on the IMD, some IMDs may be programmed to an MRI-compatible mode of operation (also referred to herein as an MRI operating mode) during the MRI scan. Typically, a clinician may program these IMDs using a programming device at some point in time prior to a scheduled MRI scan. After the patient receives the MRI scan, the clinician may reprogram the IMD back to normal settings. The reprogramming process undertaken prior to, and after, scanning a patient with an IMD may be inconvenient to both the patient and the clinician. In some scenarios, a patient having an IMD may require an emergency MRI scan. Such scenarios may not provide an adequate window of time around the MRI scan to allow for reprogramming of the IMD.

An IMD according to the present disclosure may automatically detect the presence of an MRI device (e.g., by detection of the static MRI field) prior to initiation of an MRI scan. For example, the IMD may detect the MRI device based on one or both of a strength of the magnetic field and/or a divergence in the directionality of the magnetic field. Furthermore, the IMD may differentiate the static MRI field from other magnetic fields, such as magnetic fields generated by handheld magnetic devices such as telemetry head magnets or other handheld magnets, thus improving the specificity with which the IMD identifies the source of a detected magnetic field based at least in part on the divergence in the directionality of the magnetic field.

In response to detection of the MRI device, the IMD may transition from a normal operating mode to an MRI operating mode prior to initiation of the MRI scan. While operating in the MRI mode, the IMD may be configured such that it is less susceptible to being adversely affected by the gradient and RF fields emitted by the MRI device. The capability of the IMD to automatically detect the MRI device and transition to the MRI mode may eliminate the need for manual reprogramming of the IMD prior to the MRI scan, or provide a failsafe reprogramming mode in the event manual reprogramming is not undertaken.

In one example according to the present disclosure, a device comprises a housing configured to be implanted in a patient. The device also includes a first magnetic field direction sensor located at a first location within the housing and configured to generate a signal representative of a first direction of a magnetic field at the first location, a second magnetic field direction sensor located at a second location within the housing and configured to generate a signal representative of a second direction of the magnetic field at the second location, and a magnetic field strength sensor configured to generate a signal representative of a strength of the magnetic field. A control module of the device is configured to identify a source of the magnetic field based on at least one of the signal representative of the strength of the magnetic field, the signal representative of the first direction of the magnetic field, and the signal representative of the second direction of the magnetic field.

In another example according to the present disclosure, a method comprises obtaining a signal representative of a first direction of a magnetic field at a first location within an implantable medical system, obtaining a signal representative of a second direction of a magnetic field at a second location within the implantable medical system, obtaining a signal representative of a strength of the magnetic field, and identifying a source of the magnetic field based on at least one of the signal representative of the strength of the magnetic field, the signal representative of the first direction of the magnetic field, and the signal representative of the second direction of the magnetic field.

In a further example according to the present disclosure, a non-transitory computer-readable storage medium comprising instructions that, when executed, cause a programmable processor to obtain a signal representative of a first direction of a magnetic field at a first location within an implantable medical system, obtain a signal representative of a second direction of a magnetic field at a second location within the implantable medical system, obtain a signal representative of a strength of the magnetic field, and identify a source of the magnetic field based on at least one of the signal representative of the strength of the magnetic field, the signal representative of the first direction of the magnetic field, and the signal representative of the second direction of the magnetic field.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
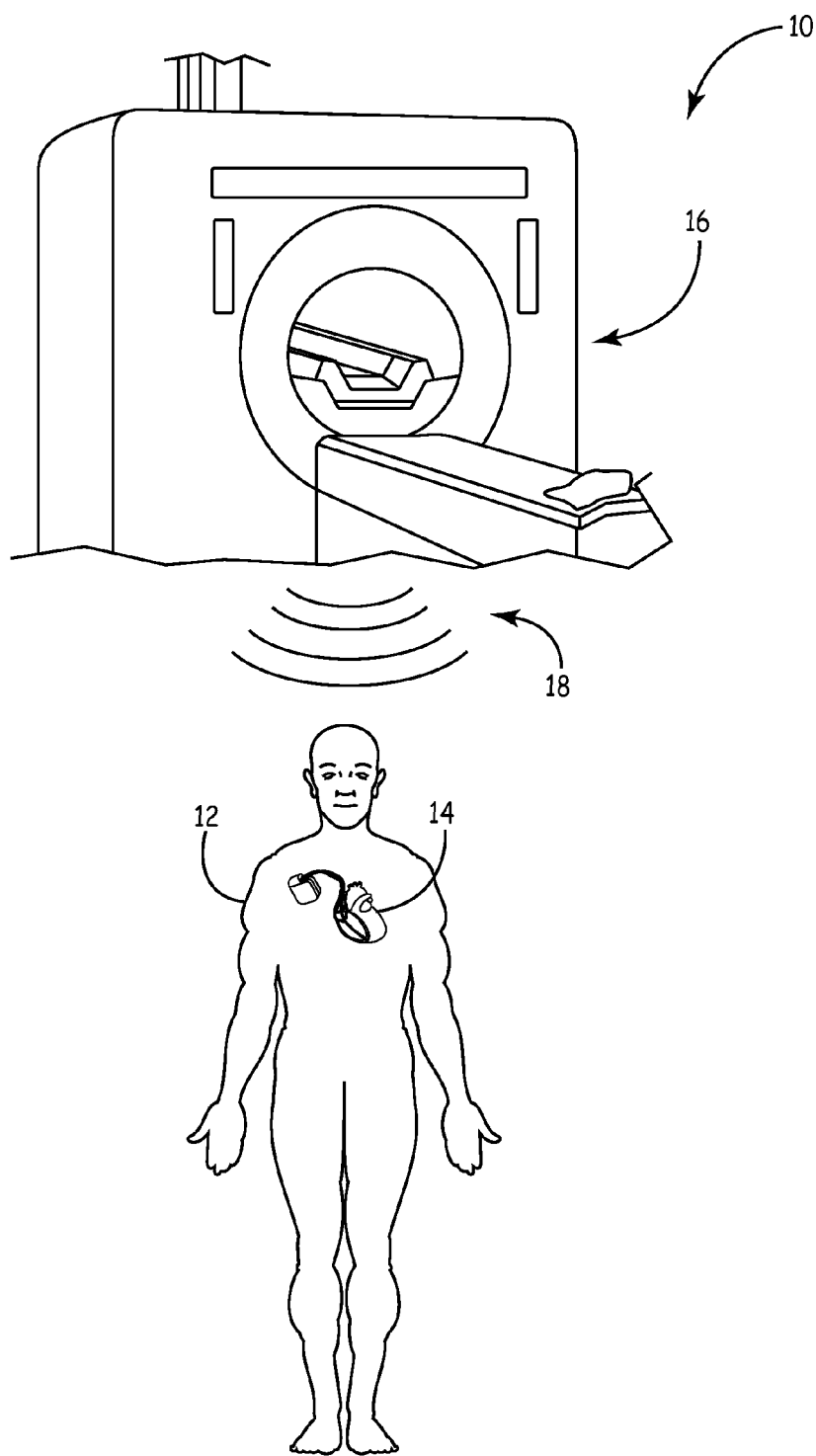
FIG. 1 is a conceptual diagram of an example magnetic resonance imaging (MRI) environment that includes an MRI device.

FIG. 1 is a conceptual diagram illustrating a magnetic resonance imaging (MRI) environment 10 that includes an MRI device 16. MRI device 16 may include a patient table on which patient 12 is placed prior to and during an MRI scan. The patient table is adjusted to position at least a portion of patient 12 within a bore of MRI device 16 (the "MRI bore"). While positioned within the MRI bore, the portion of patient 12 being scanned is subjected to a number of magnetic and RF fields to produce images of body structures for diagnosing injuries, diseases, and/or disorders.

MRI device 16 includes a scanning portion that houses a primary magnet of MRI device 16 that generates a static MRI field. The static MRI field is a large non time-varying magnetic field that is typically always present around MRI device 16 whether or not an MRI procedure is in progress. MRI device 16 also includes a plurality of gradient magnetic field coils that generate gradient magnetic fields. Gradient magnetic fields are pulsed magnetic fields that are typically only present while the MRI procedure is in progress. MRI device further includes one or more RF coils that generate RF fields. RF fields are pulsed high frequency fields that are also typically only present while the MRI procedure is in progress. Although the structure of MRI devices may vary, it is contemplated that the techniques used herein to detect the static MRI field, which is generally applicable to a variety of other MRI device configurations, such as open-sided MRI devices or other configurations.

The magnitude, frequency or other characteristic of the static MRI field, gradient magnetic fields and RF fields may vary based on the type of MRI device 16 producing the field or the type of MRI procedure being performed. A 1.5 T MRI device, for example, will produce a static magnetic field of approximately 1.5 Tesla (T) and have a corresponding RF frequency of approximately 64 megahertz (MHz) while a 3.0 T MRI device will produce a static magnetic field of approximately 3.0 Tesla and have a corresponding RF frequency of approximately 128 MHz. However, other MRI devices may generate different fields.

Patient 12 is implanted with an implantable medical system 14. In one example, implantable medical system 14 may include an IMD connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy or other therapy such as drug delivery.

Some or all of the various types of fields produced by MRI device 16 may have undesirable effects on implantable medical system 14. In one example, the gradient magnetic fields and/or the RF fields generated during the MRI procedure may induce energy on the conductors of the leads (e.g., in the form of a current). The induced energy on the leads may be conducted to the IMD and inappropriately detected as physiological signals, a phenomenon often referred to as oversensing. The detection of the induced energy on the leads as physiological signals may result in the IMD delivering therapy when it is not desired (e.g., triggering a pacing pulse) or withholding therapy when it is desired (e.g., inhibiting a pacing pulse).

Upon detecting the presence of MRI device 16, the IMD is configured to operate in an MRI operating mode or "MRI mode." Operation of the IMD in the "MRI mode" may refer to an operating state of the IMD that it is less susceptible to being adversely affected by the gradient magnetic fields and RF fields emitted by MRI device 16 than the "normal mode" of operation. As such, operation of the IMD in the MRI mode may reduce and, possibly eliminate, the undesirable effects that may be caused by the gradient magnetic fields and RF fields of MRI device 16. When operating in the MRI mode, the IMD is configured to operate with different functionality compared to the "normal mode" of operation. In one example, the IMD may operate in either a non-pacing mode (e.g., sensing only mode) or in an asynchronous pacing mode while operating in the MRI mode. The IMD may also turn off high voltage therapy (e.g., defibrillation therapy) while operating in the MRI mode. The IMD may also turn off telemetry functionality, e.g., wakeup or other telemetry activity, during operation in the MRI mode. In some examples, the MRI mode may use other sensors (e.g., a pressure or acceleration sensor), different sense circuitry, or different sense algorithms to detect cardiac activity of the patient. Other adjustments may be made as described herein. In this manner, patient 12 having implanted medical system 14 may receive an MRI procedure with a reduced likelihood of interference with operation of the IMD.

The IMD may transition to the MRI mode automatically in response to detecting MRI device 16. In accordance with the techniques of this disclosure, the IMD may detect the presence of MRI device 16 based a strength of the magnetic field and/or a divergence in the directionality of the magnetic field as measured in at least two locations within or near the IMD. In other instances, the IMD may detect the presence of MRI device 16 based on a magnitude of the static magnetic field alone. These techniques will be described in further detail herein.

After the MRI procedure is complete, the IMD may transition back to the normal mode of operation, e.g., turn high voltage therapy back on and/or have pacing that is triggered and/or inhibited as a function of sensed signals. The IMD may automatically revert to the normal mode of operation in response to no longer detecting the presence of MRI device 16, after expiration of a timer, or in response to some other predefined criteria, or a combination thereof. Alternatively, the IMD may be manually programmed into the normal mode of operation via a command received from an external device, such as programming device, via wireless telemetry.

Figure 2:
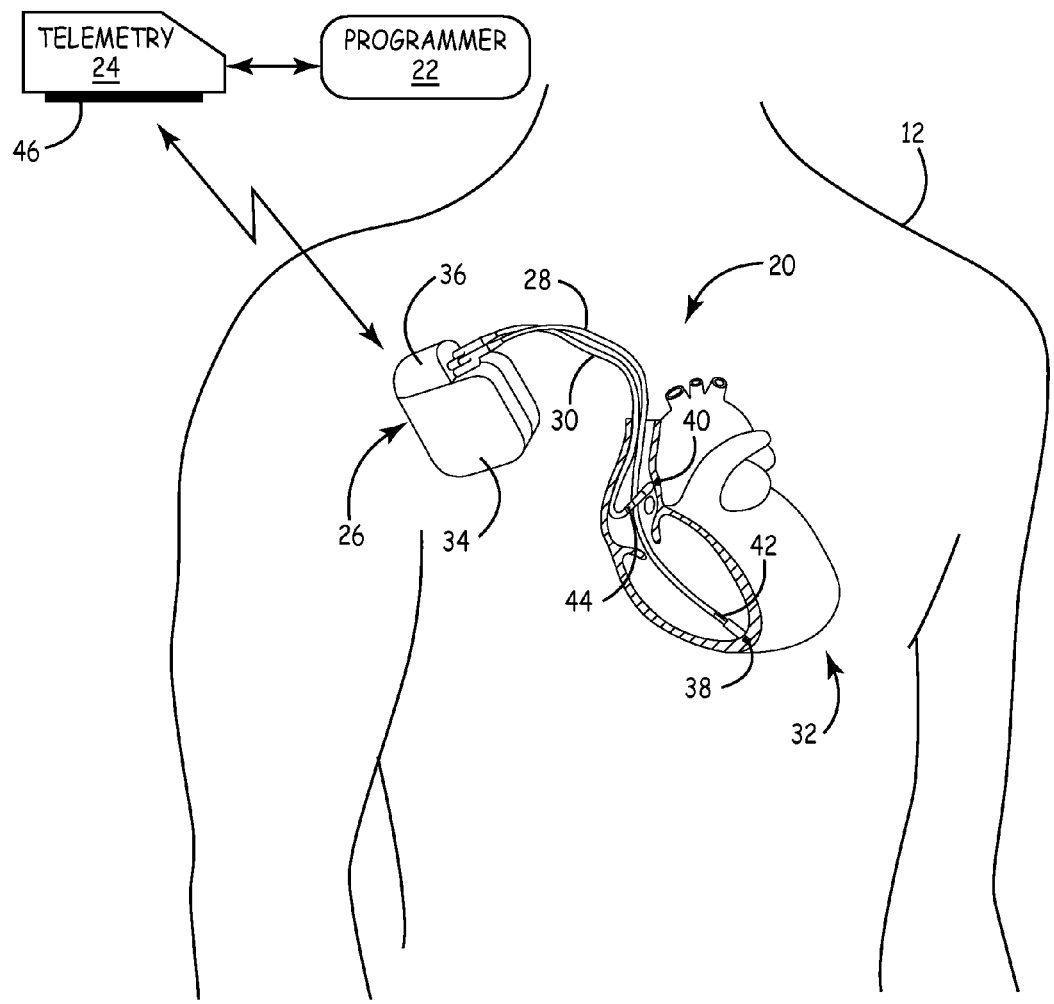
FIG. 2 is a conceptual diagram of an example medical system comprising an implantable medical device (IMD) for delivering stimulation therapy to a heart of a patient via implantable leads.
}

FIG. 2 is a conceptual diagram of an example implantable medical system 20, which may correspond with implantable medical system 14 of FIG. 1, in further detail. Implantable medical system 20 is also illustrated in conjunction with a programmer 22 and telemetry head 24. Implantable medical system 20 includes an IMD 26 connected to leads 28 and 30.

IMD 26 may be an implantable pacemaker, implantable cardioverter defibrillator (ICD), cardiac resynchronization therapy defibrillator (CRT-D), cardioverter device, or combinations thereof that provides electrical stimulation to heart 32 via leads 28 and 30. IMD 26 includes a housing 34 and a connector block 36. Housing 34 and connector block 36 may form a hermetic seal that protects components of IMD 26. In some examples, housing 34 may comprise a metal or other biocompatible enclosure having separate halves. Connecter block 36 may include electrical feedthroughs, through which electrical connections are made between conductors within leads 28 and 30 and electronic components included within housing 34. As will be described in further detail herein, housing 34 may house one or more processors, memories, transmitters, receivers, sensors, sensing circuitry, therapy circuitry and other appropriate components. Housing 34 is configured to be implanted in a patient, such as patient 12.

Leads 28 and 30 each include one or more electrodes. In the example illustrated in FIG. 2, leads 28 and 30 each include a respective tip electrodes 38 and 40 and ring electrodes 42 and 44 located near a distal end of their respective leads 28 and 30. When implanted, tip electrodes 38 and 40 and/or ring electrodes 42 and 44 are placed relative to or in a selected tissue, muscle, nerve or other location within the patient 12. In the example illustrated in FIG. 2, tip electrodes 38 and 40 are extendable helically shaped electrodes to facilitate fixation of the distal end of leads 28 and 30 to the target location within patient 12. In this manner, tip electrodes 38 and 40 are formed to define a fixation mechanism. In other embodiments, one or both of tip electrodes 38 and 40 may be formed to define fixation mechanisms of other structures. In other instances, leads 28 and 30 may include a fixation mechanism separate from tip electrode 38 and 40. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

One or more conductors (not shown in FIG. 2) extend within leads 28 and 30 from connector block 36 along the length of the lead to engage respective tip electrodes 38 and 40 and ring electrode 42 and 44. In this manner, each of electrodes 38, 40, 42 and 44 is electrically coupled to a respective conductor within its associated lead body. For example, a first electrical conductor can extend along the length of the body of lead 28 from connector block 36 and electrically couple to tip electrode 38 and a second electrical conductor can extend along the length of the body of lead 28 from connector block 36 and electrically couple to ring electrode 42. The respective conductors may electrically couple to circuitry, such as a therapy module or a sensing module, of IMD 26 via connections in connector block 36. The electrical conductors transmit therapy from a therapy module within IMD 26 to one or more of electrodes 38, 40, 42, and 44 and transmit sensed electrical signals from one or more of electrodes 38, 40, 42, and 44 to the sensing module within IMD 26.

IMD 26 may communicate with programmer 22 using any of a variety of wireless communication techniques known in the art. Examples of communication techniques may include, for example, low frequency inductive telemetry or RF telemetry, although other techniques are also contemplated. Programmer 22 may be a handheld computing device, desktop computing device, a networked computing device, or other computing device configured to communicate with IMD 26. Programmer 22 may include a non-transitory computer-readable storage medium having instructions that, when executed, cause a processor of programmer 22 to provide the functions attributed to programmer 22 in the present disclosure.

Programmer 22 retrieves data from IMD 26. Data retrieved from IMD 26 using programmer 22 may include cardiac EGMs stored by IMD 26 that indicate electrical activity of heart 32. Data may also include marker channel data that indicates the occurrence and timing of sensing, diagnosis, and therapy events associated with IMD 26. Additionally, data may include information regarding the performance or integrity of IMD 26 or other components of implantable medical system 20, such as leads 28 and 30, or a power source of IMD 26.

Programmer 22 may also transfer data to IMD 26. Data transferred to IMD 26 using programmer 22 may include, for example, values for operational parameters, electrode selections used to deliver electrical stimulation, waveform selections used for electrical stimulation, configuration parameters for detection algorithms, or the other data. Programmer 22 may also transfer lower, upper, and magnetic field divergence threshold values described herein with respect to FIGS. 4-8. These upper, lower, and magnetic field divergence threshold values may be programmable values that may be calibrated on a patient-by-patient basis, e.g., based on the type of IMD or the location/orientation of the IMD within the patient. In other examples, the values may be programmable in order to provide for compatibility with the variety of MRI devices available on the market, since different MRI devices may present different magnetic field characteristics. However, in some instances, the values may be set such that IMD 26 is capable of detecting presence of more than one MRI device using the same parameters.

Although not illustrated in FIG. 2, IMD 26 may communicate with other devices not implanted within patient 12, such as a patient monitor. The patient monitor may be a handheld computing device, desktop computing device, a networked computing device, or the like, that includes similar functionality as programmer 22. For example, the patient monitor may be a device that reads data from IMD 26 and uploads the data to a server, e.g., automatically or in response to a command from a patient or other user. Programmer 22 and the patient monitor may, but typically will not, be co-located. For example, programmer 22 may be used by a clinician in a clinical setting to communicate with IMD 26, and the patient monitor may communicate with IMD 26 in a patient's home, automatically or in response to a user command.

Programmer 22 may, in one example, communicate with IMD 26 via a telemetry head 24. Telemetry head 24 may include a telemetry head magnet 46. Telemetry head magnet 46 generates a magnetic field ("telemetry head field"). IMD 26 may detect the presence of telemetry head magnet 46 (e.g., by detecting the telemetry head field) and may operate in a telemetry head mode in response to detection of telemetry head magnet 46. Operation of IMD 26 in the "telemetry head mode" may describe a typical operating state of IMD 26 in response to detection of telemetry head magnet 46, and may be different from the MRI mode or the normal mode. For example, after IMD 26 detects telemetry head magnet 46, IMD 26 may enter the telemetry head mode and may communicate with programmer 22 or other external device by wireless telemetry via telemetry head 24 or RF telemetry or other telemetry technique, to transfer data to programmer 22 and/or receive data from programmer 22.

IMD 26 may also disable tachycardia detection when operating in the telemetry head mode.

In some examples, telemetry head magnet 46 may include a permanent magnet. The permanent magnet may have an area that is approximately equal to the area of IMD 26 so that when telemetry head 24 is placed over top of IMD 26, the permanent magnet may substantially cover IMD 26. In some examples, telemetry head magnet 46 may include handheld magnetic devices other than a permanent magnet, such as an electromagnet that generates the telemetry head field.

As described above with respect to FIG. 1, IMD 26 also operates in the MRI mode in response to detecting the static magnetic field associated with MRI device 16. As such, IMD 26 may begin operating in different operating modes in response to detecting magnetic fields from different sources, e.g., operate in the MRI mode in response to detecting the static MRI field and operate in the telemetry head mode in response to detecting the telemetry head field. To this end, IMD 26 may be configured to differentiate between magnetic fields from the different sources based on characteristics associated with the magnetic fields.

Typically, the strength (or magnitude) of the static magnetic field associated with MRI device 16 is much larger than the strength (or magnitude) of the telemetry head magnet 46 or other magnetic fields patient 12 encounters. MRI device 16 may have a static magnetic field that has a magnitude that is larger than approximately 0.5 Tesla. The strength of telemetry head magnet 46, on the other hand, is typically in the millitesla (mT) range. For example, telemetry head magnet 46 may have a magnitude in the range of approximately 10 mT to 100 mT.

However, IMD 26 may not always be capable of differentiating the source of the magnetic fields based on the magnitude or strength of the detected magnetic field alone. For example, the strength of the static MRI field decreases as a function of distance from MRI device 16. When IMD 26 is located at some distance from MRI device 16, e.g., as is the case if patient 12 is having an MRI scan of his/her ankle, there is a potential that the strength of the static MRI field at IMD 26 overlaps with the strength range associated with magnetic field strengths produced by telemetry head magnet 46. In this case, IMD 26 is unable to determine whether the magnetic field is the telemetry head field or the static MRI field.

In accordance with the techniques of this disclosure, IMD 26 may distinguish the telemetry head field from the static MRI field based on a divergence in the directionality of the magnetic field as measured in at least two locations within or near IMD 26 when the fields are indistinguishable based on the magnitude of the magnetic field alone. A divergence in the directionality of the magnetic field, as used herein, refers to a difference in directionality exhibited by a magnetic field at different locations within the magnetic field, e.g., a difference in directionality between two points in a magnetic field. Primarily due to their size, e.g., approximately the same area as IMD 26, typical magnets such as in programmer telemetry head magnet 46 produce magnetic fields that have a large divergence in directionality relative to that of the static MRI field. On the other hand, the permanent magnet of MRI device 16, which has physical dimensions that are at least an order of magnitude larger than telemetry head magnet 46, produces a magnetic field with a relatively small divergence in directionality. The field lines of the static MRI field may, for example, be essentially parallel to the bore axis from the bore opening to the end of the patient table. As will be described in further detail herein, IMD 26 may use the divergence in the directionality of the magnetic field to identify that patient 12 is within MRI environment 10 as opposed to being subjected to telemetry head magnet 46.

Although detection of telemetry head magnet 46 is described herein, the relatively large divergence in the directionality of the telemetry head field (e.g., relative to the divergence of the static MRI field) may be exhibited by other magnetic fields generated by handheld magnetic devices or other magnets that are typically encountered by patient 12. For example, a patient magnet (e.g., a handheld permanent magnet) not included in a telemetry head may generate a divergence in directionality similar to that generated by telemetry head magnet 46. Additionally, other devices that generate magnetic fields similar to telemetry head magnet 46 may come in proximity to IMD 26. Such devices may include, but are not limited to, permanent magnets and electromagnets other than the patient magnet. Telemetry head magnet 46 may, therefore, generally represent any magnetic device (e.g., handheld magnetic device) or other magnetic field source that generates a magnetic field similar to that of telemetry head magnet 46. In general, most "environmental" magnetic field sources, such as welders, electric motors, and theft detection gates, to name a few, will exhibit a magnetic field similar to that of telemetry head magnet 46, while few magnetic field sources may exhibit a magnetic field in scale as large as the permanent magnet of MRI device 16.

Although IMD 26 is illustrated as an implantable cardiac stimulation device (e.g., a pacemaker, ICD, CRT-D, or the like), in other examples, an implantable device that detects the static MRI field and operates in the MRI mode according to the present disclosure may include an implantable drug pump or an implantable neurostimulator that provides at least one of deep brain stimulation, vagus nerve stimulation, gastric stimulation, pelvic floor stimulation, spinal cord stimulation, or other stimulation. In other examples, an implantable device that detects the static MRI field and operates in the MRI mode may include any other active implantable medical device that includes electronics that the fields produced by MRI device 16 may interfere with. In other examples, a device that detects the static MRI field and operates in the MRI mode may include an external device.

Figure 3A:
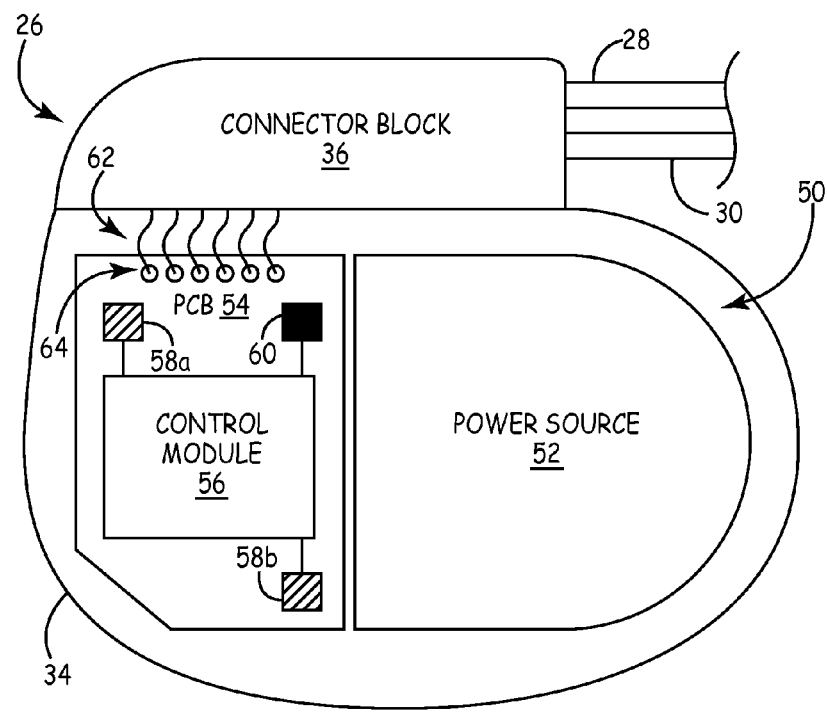
FIGS. 3A and 3B show schematic views of the IMD.
Figure 3B:
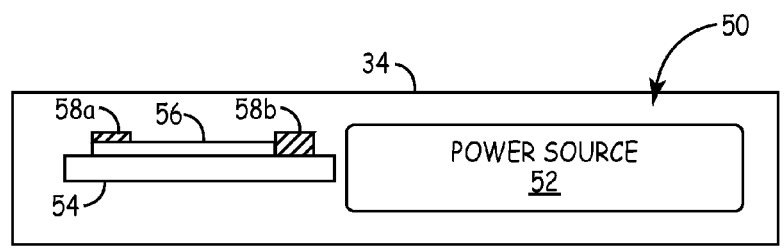

FIGS. 3A and 3B show schematic views of IMD 26. The schematic views of IMD 26 illustrate components of IMD 26 within housing 34. Housing 34 defines a cavity 50 in which components of IMD 26 are housed. FIG. 3B shows the arrangement of components within housing 34 from the bottom side of IMD 26 as illustrated in FIG. 3A.

IMD 26 includes a power source 52 housed within cavity 50. Power source 52 may include a battery, e.g., a rechargeable or non-rechargeable battery. IMD 26 includes a printed circuit board (PCB) 54 that includes electronic components of IMD 26. Electronic components include, but are not limited to, a control module 56, first and second magnetic field direction sensors 58a and 58b (collectively "magnetic field direction sensors 58"), and a magnetic field strength sensor 60.

PCB 54 may not be limited to typical PCB structures, but may instead represent any structure within IMD 26 that is used to mechanically support and electrically connect control module 56, field direction sensors 58, field strength sensor 60, power source 52, and other electronic components within housing 34. In some examples, PCB 54 may include one or more layers of conductive traces and conductive vias that provide electrical connection between control module 56, field direction sensors 58, and field strength sensor 60 as well as and electrical connection between power source 52 and control module 56, and field direction sensors 58 such that power source 52 may provide those components. Conductors within leads 28 and 30 may be connected to control module 56 on PCB 54 through connecting wires 62. For example, connecting wires 62 may be connected to conductors within leads 28 and 30 at one end (e.g., via one or more feed throughs), and connected to PCB connection points 64 on PCB 54 at the other end.

Although the electronic components of IMD 26 are illustrated as included on a single PCB, it is contemplated that the electronic components described herein may be included elsewhere within IMD 26, e.g., on other supporting structures within IMD 26, such as additional PCBs (not shown). In other examples, electronic components within IMD 26 may be mounted to the inside of housing 34 within cavity 50 or mounted to the outside of housing 34 and connected to components on the inside of housing 34 through a feed through (not shown) in housing 34. In still other examples, electronic components may be mounted on or within connector block 36 or connected to one or more of leads 28 and 30.

Control module 56, and modules included within control module 56, represents functionality that may be included in IMD 26 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. The memory may be any non-transitory computer-readable medium, including any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, the memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Field strength sensor 60 generates signals that vary as a function of a strength of the magnetic field. Field strength sensor 60 may, for example, generate and output a voltage signal that varies as a function of the strength of the magnetic field. In another example, field strength sensor 60 may only output a signal when a magnetic field exceeds a threshold field strength, as is the case for a Reed switch or other magnetic switch that closes in response to being exposed to a magnetic field of sufficient amplitude. Field strength sensor 60 may, for example, be one or more types of magnetic field sensors that may include, but are not limited to, Hall-effect sensors, giant magnetoresistance (GMR) based sensors, anisotropic magnetoresistance (AMR) based sensors, tunneling magnetoresistance (TMR) based sensors, or any other type of magnetic field sensor suitable for measuring a magnitude of a magnetic field to which it is exposed.

Each of field direction sensors 58 generate signals that vary as a function of a direction of the magnetic field applied. Thus, the signals generated by field direction sensors 58 represent the directionality of the magnetic field at the respective locations of field direction sensors 58. In particular, first field direction sensor 58a generates a signal representative of a direction of the magnetic field at the location of first field direction sensor 58a. In a similar manner, second field direction sensor 58b generates signals representative of the direction of magnetic fields at the location of second field direction sensor 58b. In other instances, IMD 26 may include more than two field direction sensors 58 that each generates signals that indicate the direction of the magnetic field at the location of respective field direction sensors 58.

Field direction sensors 58 may be any type of magnetic field sensor capable of generating signals representative of the directionality of the magnetic field. For example, field direction sensors 58 may represent one or more types of magnetic field sensors that may include, but are not limited to, Hall-effect sensors, giant magnetoresistance (GMR) based sensors, anisotropic magnetoresistance (AMR) based sensors, tunneling magnetoresistance (TMR) based sensors, or any other type of magnetic field sensor suitable for detecting a directionality of the magnetic field to which it is exposed.

One such commercially available TMR based sensor is the AAT001-10E TMR angle sensor available from NVE Corporation® of Eden Prairie, Minn. The AAT001-10E TMR angle sensor is a unique array of four TMR elements rotated at 90 degree intervals in the package and connected in a bridge configuration. Each of the sensor elements contains two magnetic layers: (1) a "pinned," or fixed direction layer and (2) a movable direction or "free" layer. The movable or free layer of the sensor elements align with the external magnetic field. As the angle between the free layer and the pinned layer changes, the resistances of the TMR elements change, which changes the output voltage of the sensor. In this manner, the output voltage of the TMR angle sensor corresponds with the angle between the fixed direction or pinned layer and the movable direction or free layer, which is representative of the direction of the magnetic field. NVE Corporation® also offers GMR-based sensors that operate using a similar technique described above. However, other commercially available sensors may also be utilized with the techniques described herein.

Each of field direction sensors 58 and/or field strength sensor 60 may include one or more axes of sensitivity. For example, field direction sensors 58 and/or field strength sensor 60 may include one axis, two axes, or three axes of sensitivity, and, therefore, field direction sensors 58 may indicate the direction of magnetic fields along one, two, or three axes and field strength sensor 60 may indicate the strength of magnetic fields along one, two, or three axes. In some examples, each of field direction sensors 58 and/or field strength sensor 60 may be single axis sensors. In other examples, each of field direction sensors 58 and/or field strength sensor 60 may be multi-axis sensors, e.g., each of field direction sensors 58 and/or field strength sensor 60 may be sensitive to magnetic fields in two or more axes. In still other examples, some of field direction sensors 58 may be multi-axis sensors, while the remaining ones of field direction sensors 58 may be single axis sensors.

It is contemplated that various configurations and number of magnetic field sensors may be implemented within IMD 26. Although two field direction sensors 58 are illustrated, IMD 26 may include more or less than two field direction sensors 58. In some examples, IMD 26 may only include one field direction sensors 58, while in other examples, IMD 26 may include three or more field direction sensors 58.

The configurations of field direction sensors 58, e.g., locations of field direction sensors 58, number of field direction sensors 58, and number of axes per field direction sensor 58, may be chosen based on various criteria. In general, a greater number of axes of sensitivity per field direction sensors 58 may result in more reliable detection of magnetic fields since a magnetic field having any orientation may be detected, whereas a single axis sensor may only measure a single axis component of the magnetic field.

In examples where a single axis sensor is used, magnetic fields having orientations that are not sensed by the single axis sensor may not be measured at the location of the single axis sensor. It therefore follows that in some examples, using multiple three axis sensors as field direction sensors 58 may provide the most complete solution to sensing any magnetic field present, regardless of direction. However, multi-axis sensors may be more costly than single axis sensors, may draw more power than single axis sensors, and control module 56 may use more processing power when polling multi-axis sensors and when determining magnetic field direction based on the signals from multi-axis sensors. Accordingly, in some examples, multi-axis sensors and single axis sensors may be arranged within IMD 26 in such a way as to provide for reliable detection the static MRI field while minimizing cost and power dissipation.

Field direction sensors 58 are mounted on PCB 54 such that each of field direction sensors 58 is oriented in the same direction. In other words, each of field direction sensors 58 is oriented such that the signals generated by field direction sensors 58 are representative of the directionality of the magnetic field relative to the same fixed direction. In the case of the GMR- or TMR-based angle sensors from NVE Corporation®, the field direction sensors 58 may be mounted such that the pinned or fixed direction layer of each of the sensors points in substantially the same direction. In this manner, the output of the sensors 58 is representative of the directionality (e.g., measured angle) relative to the same pinned or fixed direction.

Although field direction sensors 58a and 58b are illustrated as mounted on the same side of PCB 54, other arrangements of field direction sensors 58 within IMD 26 are contemplated. For example, field direction sensors 58a and 58b may be arranged on opposite sides of PCB 54 (e.g., field direction sensor 58a mounted on a top surface of PCB 54 and field direction sensor 58b mounted on a bottom surface of PCB 54). In instances in which IMD 26 includes more than two field direction sensors 58, field direction sensors 58 may be arranged on the same side of PCB 54 or on different sides of PCB 54. The placement and spacing of the sensors would depend on the resolution of the sensors and the differences in divergence in the fields IMD 26 would need to distinguish. In further examples, field direction sensors 58 may be included on the same integrated circuit substrate and therefore packaged within the same integrated circuit package. In some examples, the field direction sensors 58 may be included within integrated circuit packages along with other electronics components, e.g., on substrates with other integrated circuits or packaged with other integrated circuits within a multi-chip package.

IMD 26 may be subjected to various sources of magnetic fields having different characteristics. For example, IMD 26 may be subjected to the telemetry head field of telemetry head magnet 46 or the static MRI field of MRI device 16. Control module 56 may identify the source of a detected magnetic field based on signals received from one or more of field direction sensors 58, field strength sensor 60, or a combination thereof. For example, based on signals received from one or more of field direction sensors 58 and/or field strength sensor 60, control module 56 may identify the source of the detected magnetic field as the primary magnet of MRI device 16 or telemetry head magnet 46. A processor of control module 56 may then operate IMD 26 in the MRI mode when the source is identified as the primary magnet of MRI device 16 or the telemetry head mode when the source is identified as telemetry head magnet 46.

In some instances, control module 56 may operate IMD 26 in a generic magnet mode in response to the magnitude of the magnetic field exceeding a strength threshold and then transition to the MRI mode operate IMD 26 in the MRI mode when the source is identified as the primary magnet of MRI device 16 or the telemetry head mode when the source is identified as telemetry head magnet 46. In one example, the generic magnet mode may be the same as the telemetry head mode.

In some examples, control module 56 may identify the source of the detected magnetic field based on both a strength of the detected magnetic field and divergence in the directionality of the magnetic field as measured in at least two locations within or near IMD 26. In other examples, control module 56 may identify the source of the detected magnetic field based on the divergence in the directionality of the magnetic field in addition to detected parameters other than magnetic field strength, such as a detected frequency of RF fields to which IMD 26 is subjected, detected gradient magnetic fields to which IMD 26 is subjected, saturation of a transformer core, or the like.

Figure 4:
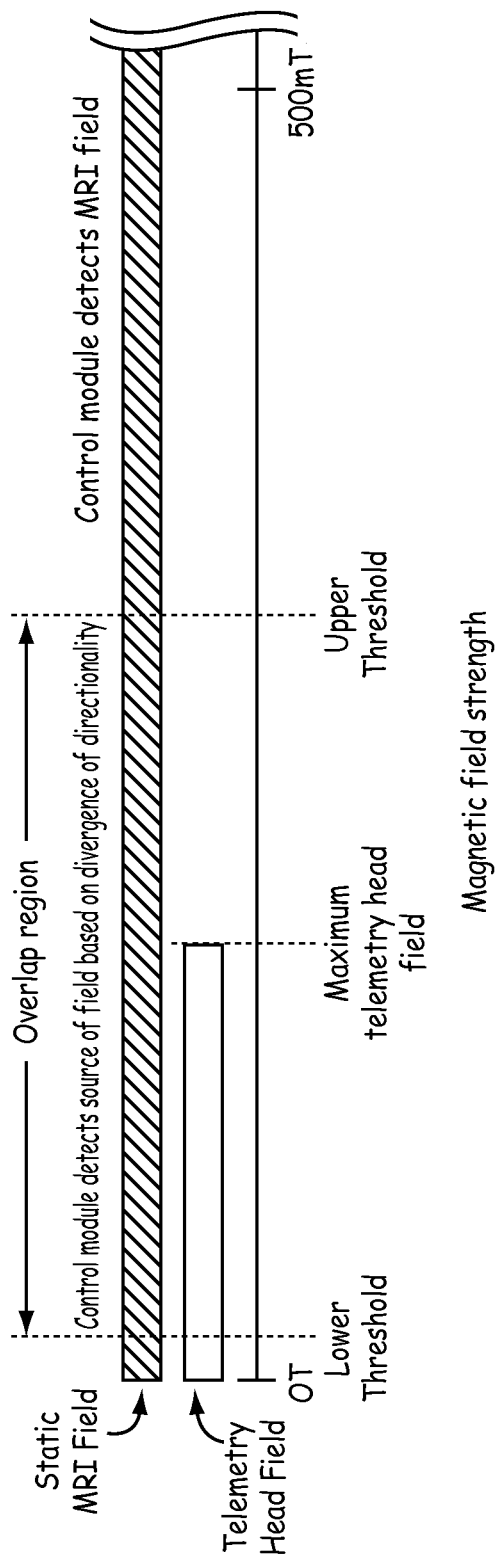
FIG. 4 shows the strength ranges of a static MRI field and a telemetry head field relative to example strength thresholds.

Detection of the various fields based on strength and divergence in the directionality of the static MRI field and telemetry head field is now discussed with reference to FIG. 4. Strength of the telemetry head field and the static MRI field are illustrated in FIG. 4 as the shaded box and hashed box, respectively, along with programmable thresholds (e.g., lower and/or upper thresholds) used by control module 56 to determine the source of detected magnetic fields.

The strength of the telemetry head field may be at a maximum at a point nearest to telemetry head magnet 46. The strength of the telemetry head field may decrease (e.g., exponentially) with increasing distance from telemetry head magnet 46. In FIG. 4, the strength of the telemetry head field is illustrated as ranging from 0 T up to the demarcated "maximum telemetry head field." The maximum telemetry head field may be a maximum strength of the telemetry head field, e.g., at a point closest to telemetry head magnet 46.

At a short distance from telemetry head magnet 46 (e.g., within inches), the telemetry head field may drop significantly in strength, e.g., sometime as low as 0-1 mT. For example, within inches (e.g., less than 10 inches), the telemetry head field may drop to less than 0.5 mT. The left edge of the solid shaded region at 0 T indicates a scenario where the telemetry head field is not detectable by field strength sensor 60. In other words, the far left edge of the solid shaded region at 0 T indicates a scenario where IMD 26 is positioned relative to telemetry head magnet 46 such that the field generated by telemetry head magnet 46 is not detectable by field strength sensor 60. As the distance between telemetry head magnet 46 and IMD 26 is decreased (telemetry head magnet 46 is closer to IMD 26), the strength of the telemetry head field detectable by field strength sensor 60 may increase up to the maximum telemetry head field.

In some examples, the strength of the maximum telemetry head field detectable by one of field strength sensor 60 may be approximately 100 mT, e.g., when IMD 26 is in close proximity to telemetry head magnet 46. Although the maximum telemetry head field may be approximately 100 mT in some instances, in other examples, the maximum telemetry head field may be greater or less than 100 mT.

The strength of the static MRI field may reach a maximum value within the MRI bore (e.g., close to the primary magnet) of the MRI device and taper off towards a value of 0 T in areas outside of the MRI bore. Generally, the static MRI field decreases in strength with increasing distance from the MRI bore. The left edge of the hashed region at 0 T indicates a scenario where the static MRI field is not detectable by field strength sensor 60. In other words, the far left edge of the hashed region at 0 T indicates a scenario where IMD 26 is positioned relative to the MRI bore such that the static MRI field generated by MRI device 16 is not detectable by field strength sensor 60. As the distance between the MRI bore and IMD 26 is decreased (IMD 26 is closer to the MRI bore), the strength of the static MRI field detectable by field strength sensor 60 may increase up to the maximum strength of the static MRI field, which is typically greater than 0.5 T and, in the case of the majority of the MRI devices on the market today, either approximately 1.5 T or 3.0 T (although MRI devices with static MRI fields greater than and less than these values are available). The far right portion of the hashed region in FIG. 4 illustrates the magnetic field detectable by field strength sensor 60 when IMD 26 is positioned near to, or within, the MRI bore.

The values labeled as "lower threshold" and "upper threshold" in FIG. 4 may be programmable values stored in control module 56 or a memory within IMD 26 that may be used by control module 56. The lower threshold may be a value indicating a minimum magnetic field strength which control module 56 may identify as either telemetry head field or as static MRI field. When the detected magnetic field is weaker than the lower threshold, control module 56 may operate IMD 26 in the normal mode. The lower threshold value may be set to a value that reliably indicates that IMD 26 is exposed to a magnetic field, such as a reliable indication that telemetry head magnet 46 is near to IMD 26 or that MRI device 16 is near to IMD 26. In other words, the lower threshold value may be set so that control module 56 ignores magnetic fields that are weaker than may be indicative of telemetry head magnet 46 or MRI device 16. The lower threshold value may be programmed such that control module 56 rejects "noise" or magnetic fields produced by sources other than telemetry head magnet 46 or MRI device 16. In some examples, the lower threshold may be set to approximately 1-2 mT.

The upper threshold value indicates a maximum magnetic field strength that control module 56 may recognize as a magnetic field generated by telemetry head magnet 46. Control module 56 may determine that IMD 26 is in the presence of the static MRI field when the detected magnetic field is greater than the upper threshold. For example, the upper threshold value may be set such that the upper threshold value is greater than a magnetic field that is producible by telemetry head magnet 46 or any other common environmental magnetic field source. Accordingly, detection of a magnetic field above the upper threshold value may indicate with high probability that the detected magnetic field is generated by the primary magnet of MRI device 16, and not telemetry head magnet 46. Therefore, in examples where control module 56 detects a magnetic field having a strength greater than the upper threshold value, control module 56 may reliably identify the source of the detected magnetic field as the primary magnet of MRI device 16. Control module 56 may then operate IMD 26 in the MRI mode.

In some examples, the upper threshold value may be set to approximately 200-500 mT, e.g., a range of magnetic field strengths not producible by conventional telemetry head magnets, or at least not typically producible by conventional telemetry head magnets at a location where IMD 26 is implanted. However, strength of the telemetry head field may vary amongst telemetry head magnets, and accordingly, in some examples, setting the upper threshold value to a value that is only slightly greater (e.g., by 200-500 mT) than the maximum telemetry head field may not be sufficient to reliably rule out the telemetry head field. Therefore, selection of an upper threshold value that is substantially greater (e.g., by a factor of 2) than may be producible by most conventional telemetry head magnets may result in more reliable detection of the static MRI field based solely on the magnitude of the detected magnetic field at a single location.

Depending on the location of IMD 26 relative to the magnetic field source the strength of the static MRI field may be similar to the strength of the telemetry head field. For example, when IMD 26 is located a distance away from the MRI bore, e.g., on the order of 1-2 feet, depending on the strength of the permanent magnet, the static MRI field may have a similar strength as fields produced by telemetry head magnet 46 (e.g., 100 mT or less). In this case, control module 56 may not reliably differentiate the static MRI field from the telemetry head field based on the strength of the detected magnetic field alone. The range of values between the upper and lower threshold values which includes magnetic field strengths that may be indicative of either the telemetry head field or the static MRI field may be referred to as the "overlap region," as indicated in FIG. 4.

In other instances, field strength sensor 60 may only be capable of producing a binary output, e.g., a first output when no magnetic field is detected and a second output when a magnetic field exceeding a threshold is detected. For example, magnet field strength sensor 60 may be a Reed switch or other magnetic sensor only capable of determining whether a magnetic field exceeds a single threshold, such as the lower threshold discussed above. In this case, control module 56 would not be capable of distinguishing the source of the magnetic field based on magnitude or strength alone. However, control module 56 would be able to determine the presence of an external magnetic field having a magnitude that exceeds the threshold of the magnetic field sensor, which may be equal to the lower threshold, upper threshold, or threshold value somewhere between the described lower and upper thresholds. In such an example, the "overlap region" may correspond to the entire region above the single threshold, such as the lower threshold illustrated in FIG. 4.

Figure 5A:
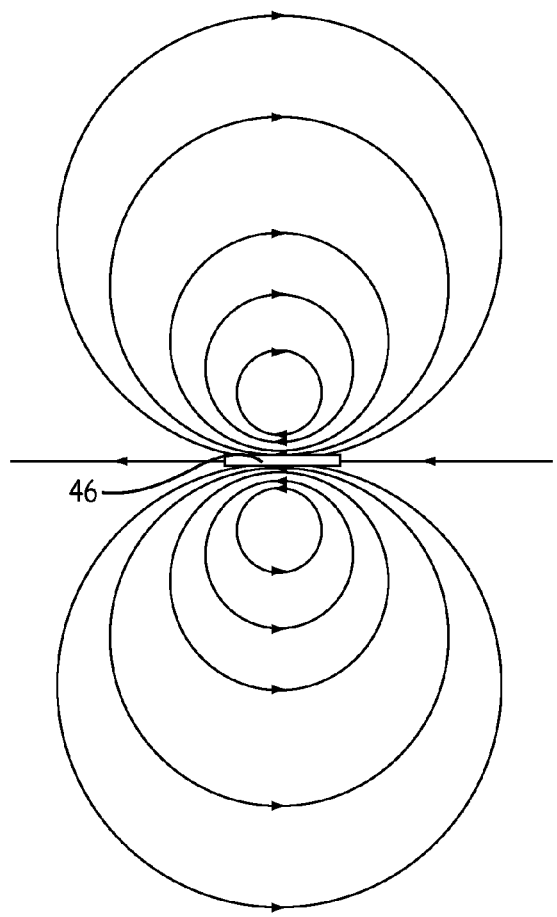
FIGS. 5A and 5B are conceptual diagrams illustrating example magnetic field lines of a telemetry head magnet and a primary magnet of an MRI device, respectively.
Figure 5B:
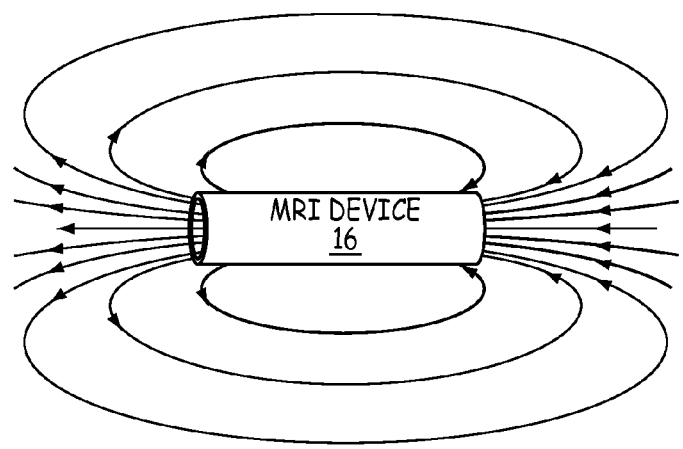

Although the static MRI field and the telemetry head field may have similar strengths in the overlap region, the divergence in the directionality of the magnetic fields produced by the static MRI field and the telemetry head field as measured at two or more locations within or near IMD 26 may differ from each other. FIGS. 5A and 5B illustrate example magnetic field patterns for telemetry head magnet 46 and MRI device 16, respectively. FIGS. 5A and 5B are provided as exemplary field patterns and are not drawn to scale. As described above with respect to FIG. 2, telemetry head magnet 46 typically has an area that is approximately equal to the area of IMD 26 so that when telemetry head 46 is placed over top of IMD 26, telemetry head magnet 46 substantially covers IMD 26. On the other hand, the static magnet of MRI device 16 is much larger in size, e.g., typically at least an order of magnitude larger than telemetry head magnet 46 and in most instances two or more orders of magnitude larger. For example, the bore of an MRI scanner may be between 60-72 centimeters (cm) while a typical telemetry head magnet is approximately 6 cm. Primarily due to the difference in the physical dimensions of the magnets, the divergence in the directionality at field direction sensors 58a and 58b is much larger when IMD 26 is exposed to telemetry head magnet 46 than the divergence in the directionality at field direction sensors 58a and 58b when IMD 26 is exposed to the static MRI field.

Magnetic field lines from the bore of MRI device 16 to the end of the patient table may be essentially parallel to the bore axis and thus essentially parallel to one another. As such, divergence when the patient is on the patient table will be fairly small. There are regions near MRI device 16 where the divergence in directionality of the field may be large, such as near the scanner bore opening. However, in these regions, the magnitude of the static field will also be large. The magnetic field lines of telemetry head magnet 46, on the other hand, change directions within a much smaller area causing a much larger divergence in the directionality as measured within or near IMD 25.

Control module 56 may determine a parameter indicative of a directionality of the magnetic field to which IMD 26 is exposed based on the signals obtained from field direction sensors 58. For example, control module 56 may determine, for each of field direction sensors 58, an angle of the magnetic field relative to a fixed direction based on the signal output by magnetic field sensor. In the case of a GMR- or TMR-based angle sensor available from NVE Corporation®, control module 56 may determine, for each field direction sensor 58, an angle between a "pinned" or fixed direction layer and a movable direction or "free" layer based on the voltage signal output by the sensor. In other examples, control module 56 may determine one or more parameters indicative of directionality of the magnetic field other than an angle relative to a fixed direction.

Control module 56 determines a divergence in the directionality of the magnetic field based on the measured parameters indicative of the directionality of the magnetic field. In one example, control module 56 may determine an absolute difference between the angles measured at the respective locations of field direction sensors 58. In general, the difference between the directionality of the magnetic field of the telemetry head magnet 46 as measured at the respective locations of field direction sensors 58 is greater than the difference between the directionality of the magnetic field of the static MRI field as measured at the respective locations of field direction sensors 58. In other words, the divergence in the directionality is larger for telemetry head magnet 46 than for the permanent magnet of MRI device 16. This is particularly true when the strength of the detected magnetic field is within the overlap region.

Control module 56 may compare the determined absolute difference to a field divergence threshold value that reliably demarcates the range of magnetic field divergence values that indicate the static MRI field and the range of magnetic field divergence values that indicate the telemetry head field. For example, the magnetic field divergence threshold value may be selected such that measured magnetic field divergence values less than the magnetic field divergence threshold indicate the static MRI field, while magnetic field divergence values greater than the magnetic field divergence threshold value indicate the telemetry head field. The magnetic field divergence threshold value may be set by the user in some examples using programmer 22.

In one example, control module 56 may use the divergence in the directionality of the magnetic field in order to differentiate between the static MRI field and the telemetry head field in the overlap region. When control module 56 detects a magnetic field having a strength in the overlap region discussed above with respect to FIG. 4, control module 56 may determine the divergence in the directionality of the sensed magnetic field, e.g., the difference in the directionality of the magnetic field sensed at field direction sensors 58. Subsequently, control module 56 may compare the determined divergence in the directionality of the magnetic field to the field divergence threshold. Control module 56 may identify the source of the detected magnetic field as telemetry head magnet 46 when the divergence in the directionality of the magnetic field is greater than the field divergence threshold and identify the source of the detected magnetic field as the primary magnet of MRI device 16 when the divergence in the directionality of the magnetic field is less or equal to the field divergence threshold. In some instances, the overlap region may be entire region above a threshold magnetic field strength, as is the case for a magnetic strength sensor 60 that is not capable of distinguishing magnetic fields of different strengths above the single threshold.

Field direction sensors 58 may, in some instances, only be utilized upon detecting a magnetic field that exceeds the lower threshold value. For example, field direction sensors 58 may be turned on in response to detecting a magnetic field that exceeds the lower threshold value. Control module 56 may include circuitry for selectively providing power to field direction sensors 58. Prior to detection of the magnetic field exceeding the lower threshold value, field direction sensors 58 may remain off, such that no power is consumed. In this manner, only field strength sensor 60 is on or active until a magnetic field is detected, thereby reducing power consumption by sensor 58 and processing resources that are necessary for processing the outputs of field direction sensors 58. In another example, control module 56 may provide power to field direction sensors 58 only after determining that the source of the magnetic field cannot be detected using the measured strength of the magnetic field alone, e.g., in response to the determining that the magnetic field falls within the overlap region.

Figure 6:
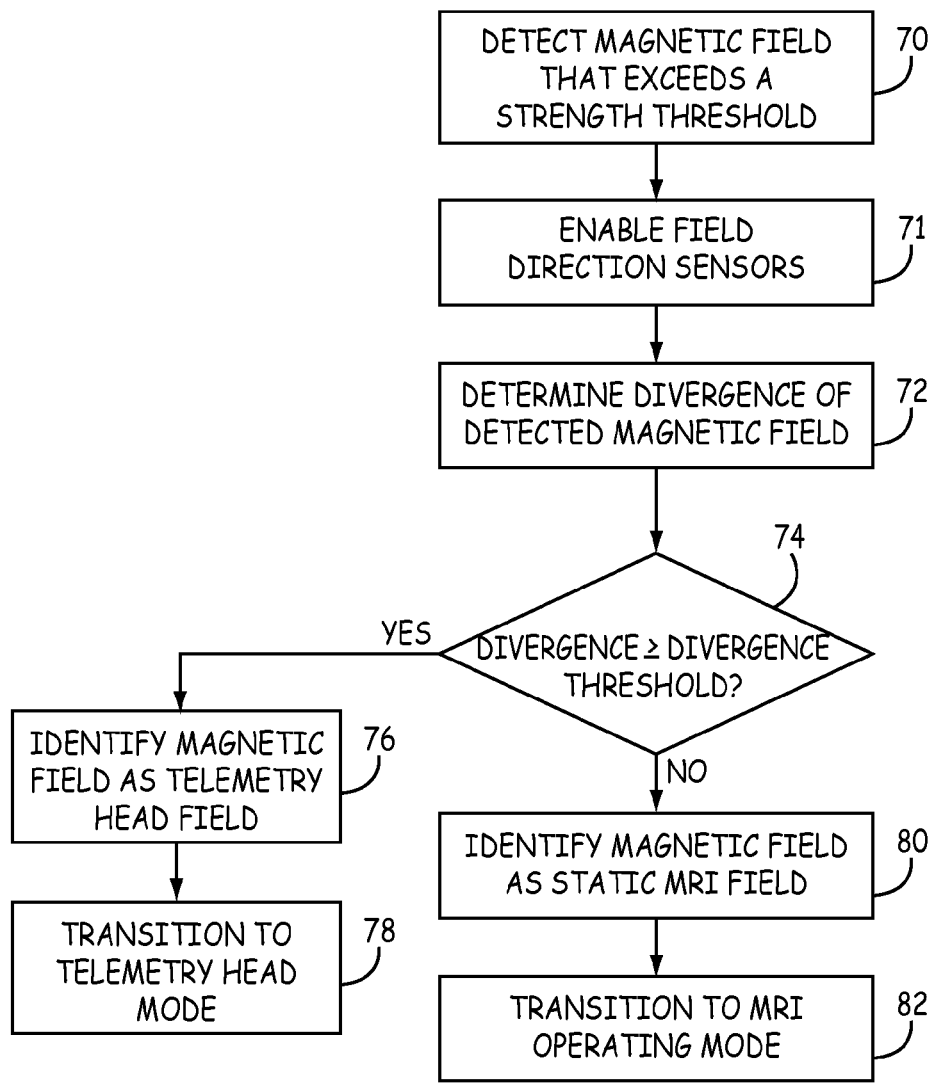
FIG. 6 is a flow diagram of an example method for differentiating between a static MRI field and a telemetry head field.

FIG. 6 is a flow diagram that illustrates an example method for identifying a source of a magnetic field according to one aspect of the present disclosure. Initially, control module 56 determines a magnetic field that exceeds a magnetic field strength threshold (70). Control module 56 may determine the strength of the magnetic field based on signals received from field strength sensor 60.

In response to determining that the strength of the magnetic field exceeds the strength threshold, control module 56 may enable field direction sensors 58 to measure a directionality of the magnetic field (71). In the example IMD 26 of FIGS. 3A and 3B, which has two field direction sensors 58, a first field direction sensor 58a generates a signal representative of a direction of the magnetic field at the location of first field direction sensor 58a and the second field direction sensor 58b generates signals representative of the direction of magnetic fields at the location of second field direction sensor 58b. In other instances, IMD 26 may include more than two field direction sensors 58 that each generates signals that indicate the direction of the magnetic field at the location of respective field direction sensors 58.

Control module 56 may determine the divergence in the directionality of the detected magnetic field (72). Control module 56 obtains the signals generated by field direction sensors 58 and determines the directionality of the magnetic field at each of the locations of magnetic field sensors based on the signals obtained from the respective one of field direction sensors 58. In one example, control module 56 determines an angle of the magnetic field relative to a fixed direction at the location of each of field direction sensors 58. Using the determined angles of the magnetic field at the various locations (or other parameter indicative of the directionality of the magnetic field at those locations), control module 56 determines the divergence of the detected magnetic field, e.g., by computing an absolute difference between the angle at magnetic field sensor 58*a* and the angle of the magnetic field at magnetic field sensor 58*b*.

In some instances in which IMD 26 includes more than two field direction sensors 58, control module 56 may determine the absolute difference between each of the angles measured at the location of all magnetic field sensors. In the case of three field direction sensors 58, for example, control module 56 may determine the absolute difference between the angle measured at the first sensor and the angle measured at the second sensor, the absolute difference between the angle measured at the first sensor and the angle measured at the third sensor, and the absolute difference between the angle measured at the second sensor and the angle measured at the third sensor. Control module 56 may determine the divergence in the magnetic field based on one or more of the absolute differences. In one example, control module 56 may select the largest computed absolute difference as the divergence in the directionality of the magnetic field. In another example, control module 56 may average the computed absolute differences and use the average as the divergence in the directionality of the magnetic field.

Control module 56 compares the determined divergence in the magnetic field to a divergence threshold (74). As described above, the magnetic field divergence threshold may be programmed by the user in some examples using programmer 22. When the determined divergence in the magnetic field is greater than or equal to the divergence threshold, control module 56 identifies the magnetic field as the telemetry head field (76) and control module 56 transitions IMD 26 from operation in the normal mode to operation in the telemetry head mode (78). When the determined divergence in the magnetic field is not greater than or equal to (i.e., is less than) the divergence threshold, control module 56 identifies the magnetic field as the static MRI field (80) and control module 56 transitions IMD 26 from operation in the normal mode to operation in the MRI mode (82).

Figure 7:
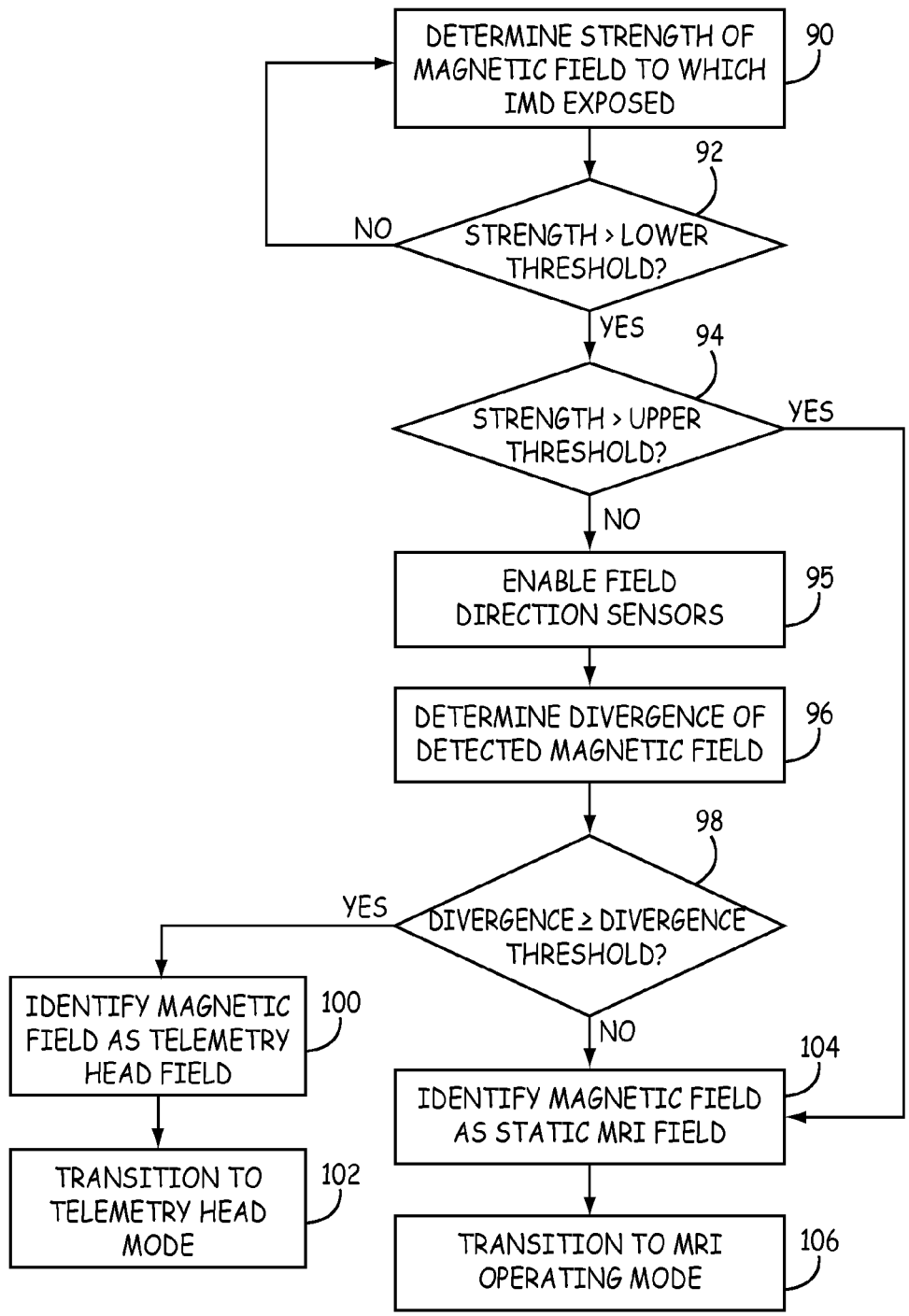
FIG. 7 is a flow diagram of another example method for differentiating between a static MRI field and a telemetry head field.

FIG. 7 is a flow diagram that illustrates another example method for identifying a source of a magnetic field according to another aspect of the present disclosure. Initially, control module 56 may determine the strength of a magnetic field in which IMD 26 is located (90). Control module 56 may determine the strength of the magnetic field based on one or more signals received from magnetic field sensor 60. For example, magnetic field sensor 60 may be a Hall effect sensor that outputs a voltage that varies as a function of the strength of the magnetic field and control module 56 may determine the strength of the magnetic field based on the voltage from the sensor.

Control module 56 determines whether the strength of the magnetic field determined in block (90) is greater than the lower threshold (92). As described above with respect to FIG. 4, the lower threshold may be a value indicating a minimum magnetic field strength which control module 56 may identify as either telemetry head field or as static MRI field. If the strength of the magnetic field is not greater than the lower threshold, control module 56 continues to monitor the strength of the magnet field in which IMD 26 is located in block (90) until the strength of the magnetic field is greater than the lower threshold value.

If the strength of the magnetic field determined in block (90) is greater than the lower threshold, control module 56 determines whether the strength of the magnetic field is greater than the upper threshold (94). The upper threshold value indicates a maximum magnetic field strength that control module 56 may recognize as a magnetic field generated by telemetry head magnet 46. If the strength of the magnetic field is greater than the upper threshold, control module 56 identifies the magnetic field as the static MRI field (104) and control module 56 may transition IMD 26 from operation in the normal mode to operation in the MRI mode to prepare IMD 26 for an MRI scan (106).

If the strength of the magnetic field is not greater than the upper threshold, and therefore between the lower threshold and the upper threshold (i.e., in the overlap region), control module 56 may enable (e.g., power up) field direction sensors 58 to measure a directionality of the magnetic field (95). In the example IMD 26 of FIGS. 3A and 3B, which has two field direction sensors 58, a first field direction sensor 58*a* generates a signal representative of a direction of the magnetic field at the location of first field direction sensor 58*a* and the second field direction sensor 58*b* generates signals representative of the direction of magnetic fields at the location of second field direction sensor 58*b*. In other instances, IMD 26 may include more than two field direction sensors 58 that each generates signals that indicate the direction of the magnetic field at the location of respective field direction sensors 58.

Control module 56 determines the divergence in the directionality of the detected magnetic field (96). As described above, control module 56 obtains signals from field direction sensors 58 and determines the directionality of the magnetic field at each of the locations of magnetic field sensors based on the signals obtained from the respective one of field direction sensors 58. In one example, control module 56 determines an angle of the magnetic field relative to a fixed direction at the location of each of field direction sensors 58. Using the determined angles of the magnetic field at the various locations (or other parameter indicative of the directionality of the magnetic field at those locations), control module 56 determines the divergence of the detected magnetic field, e.g., by computing an absolute difference between the angle at magnetic field sensor 58*a* and the angle of the magnetic field at magnetic field sensor 58*b*.

In some instances in which IMD 26 includes more than two field direction sensors 58, control module 56 may determine the absolute difference between each the angles measured at the location of all magnetic field sensors. In the case of three field direction sensors 58, for example, control module 56 may determine the absolute difference between the angle measured at the first sensor and the angle measured at the second sensor, the absolute difference between the angle measured at the first sensor and the angle measured at the third sensor, and the absolute difference between the angle measured at the second sensor and the angle measured at the third sensor. Control module 56 may determine the divergence in the magnetic field based on one or more of the absolute differences. In one example, control module 56 may select the largest computed absolute difference as the divergence in the directionality of the magnetic field. In another example, control module 56 may average the computed absolute differences and use the average as the divergence in the directionality of the magnetic field.

Control module 56 compares the divergence determined in block (96) to a magnetic field divergence threshold (98). As described above, the magnetic field divergence threshold may be programmed by the user in some examples using programmer 22. When the magnetic field divergence is greater than or equal to the magnetic field divergence threshold, control module 56 identifies the magnetic field as the telemetry head field (100) and control module 56 transitions IMD 26 from operation in the normal mode to operation in the telemetry head mode (102). When the magnetic field divergence is not greater than or equal to (i.e., is less than) the magnetic field divergence threshold, control module 56 identifies the magnetic field as the static MRI field (104) and control module 56 transitions IMD 26 from operation in the normal mode to operation in the MRI mode (106).

In some instances, control module 56 may operate IMD 26 in a generic magnet mode in response to the magnitude of the magnetic field exceeding a strength threshold and then transition to the MRI mode operate IMD 26 in the MRI mode when the source is identified as the primary magnet of MRI device 16 or the telemetry head mode when the source is identified as telemetry head magnet 46. For example, control module 56 may begin operation in the generic magnet mode when the magnetic field exceeds the lower threshold, but does not exceed the upper threshold. In one example, the generic magnet mode may be the same as the telemetry head mode.

Figure 8:
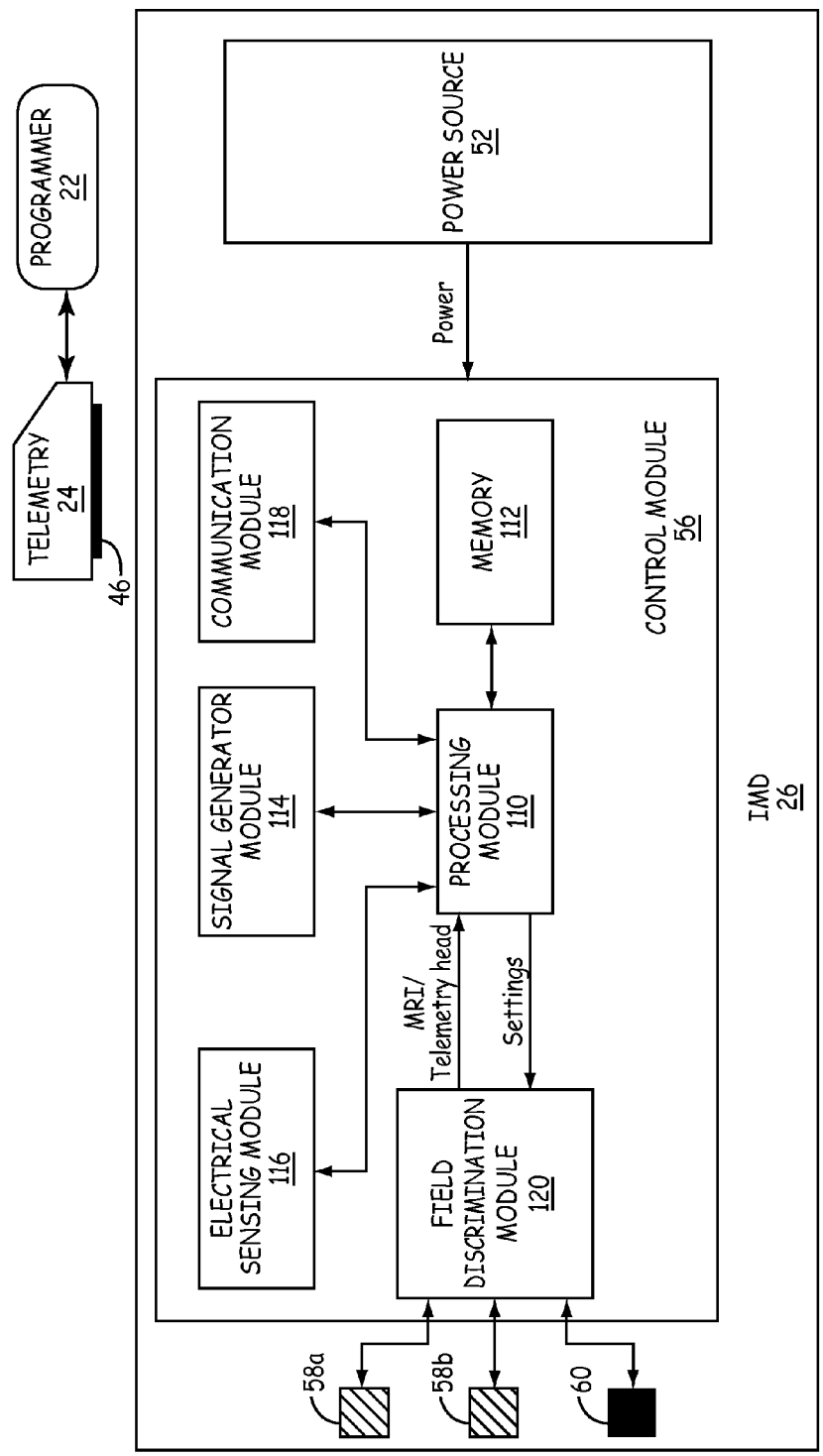
FIG. 8 is a functional block diagram that illustrates an example control module of the IMD.

FIG. 8 is a block diagram that illustrates an example control module 56 of IMD 26 in further detail. Control module 56 includes a processing module 110, memory 112, a therapy module 114, a sensing module 116, a communication module 118, and a field discrimination module 120.

Processing module 110 may communicate with memory 112. Memory 112 may include computer-readable instructions that, when executed by processing module 110, cause processing module 110 to perform the various functions attributed to processing module 110 herein. Memory 112 may be any non-transitory computer-readable medium, including any volatile, non-volatile, magnetic, or electrical media, such as RAM, ROM, NVRAM, EEPROM, Flash memory, or any other digital media.

Processing module 110 may also communicate with therapy module 114 and sensing module 116. Therapy module 114 and sensing module 116 are electrically coupled to electrodes 38, 40, 42, and 44 of leads 28 and 30. Sensing module 116 is configured to analyze signals from electrodes 38, 40, 42, and 44 of leads 28 and 30 in order to monitor electrical activity of heart 102, such as the depolarization and repolarization of heart 102. Processing module 110 may detect cardiac activity based on signals received from electrical sensing module 110. In some examples, processing module 110 may detect tachyarrhythmias based on signals received from sensing module 116, e.g., using any suitable tachyarrhythmia detection algorithm.

Processing module 110 may generate EGM waveforms based on the detected cardiac activity. Processing module 110 may also generate marker channel data based on the detected cardiac activity. For example, marker channel data may include data that indicates the occurrence and timing of sensing, diagnosis, and therapy events associated with IMD 26. Additionally, marker channel data may include information regarding the performance or integrity of components of IMD 26 or leads 28 and 30. Processing module 110 may store EGM waveforms and marker channel data in memory 112. Processing module 110 may later retrieve stored EGMs from memory 112, e.g., upon a request from programmer 22 via communication module 118.

Therapy module 114 is configured to generate and deliver therapy, such as electrical stimulation therapy, to heart 102 or other desired location. Processing module 110 may control therapy module 114 to deliver electrical stimulation therapy to heart 102 according to one or more therapy programs, which may be stored in memory 112. For example, processing module 110 may control therapy module 114 to deliver pacing pulses to heart 102 based on one or more therapy programs and signals received from sensing module 116.

Therapy module 114 may also be configured to generate and deliver cardioversion and/or defibrillation shocks to heart 102 in addition to or instead of pacing pulses. Processing module 110 may control therapy module 114 to deliver the cardioversion and defibrillation pulses to heart 102. For example, in the event that processing module 110 detects an atrial or ventricular tachyarrhythmia, processing module 110 may load an anti-tachyarrhythmia pacing regimen from memory 112, and control therapy module 114 to implement the anti-tachyarrhythmia pacing regimen. Therapy module 114 may include a high voltage charge circuit and a high voltage output circuit when therapy module 114 is configured to generate and deliver defibrillation pulses to heart 102, e.g., should the ATP therapy not be effective to eliminate the tachyarrhythmia.

Communication module 118 includes any suitable hardware, firmware, software or any combination thereof for communicating with another device, such as programmer 22 and/or a patient monitor, e.g., by wireless telemetry. Under the control of processing module 110, communication module 118 may receive downlink telemetry from and send uplink telemetry to programmer 22 and/or a patient monitor with the aid of an antenna (not shown) in IMD 26. Processing module 110 may provide the data to be uplinked to programmer 22 and the control signals for a telemetry circuitry within communication module 118.

In some examples, IMD 26 may include additional sensors other than field direction sensors 58 or field strength sensor 60, with which processing module 110 may communicate. For example, IMD 26 may include one or more of a motion sensor (e.g., an accelerometer or piezoelectric element), a heart sound sensor, or a pressure sensor (e.g., a capacitive sensor) that senses intracardiac or other cardiovascular pressure. The one or more additional sensors may be located within housing 34, outside of housing 34, attached to one or more of leads 28 or 30, or wirelessly coupled to control module 56 via communication module 118. In some examples, field direction sensors 58 or field strength sensor 60 may be located outside of housing 34, attached to one or more of leads 28 or 30, or wirelessly coupled to control module 56 via communication module 118.

Field discrimination module 120 communicates with field direction sensors 58, field strength sensor 60, and processing module 110. Field discrimination module 120 may include circuits that interface with field direction sensors 58 and field strength sensor 60. For example, field discrimination module 120 may include circuits that provide power to field direction sensors 58 and field strength sensor 60, or amplification circuits, filtering circuits, and/or other signal conditioning circuits that process signals received from field direction sensors 58 and field strength sensor 60. In some examples, field discrimination module 120 may also include circuits that digitize the conditioned signals and communicate the digitized signals to processing module 110.

Field discrimination module 120 receives signals from field strength sensor 60 and determines the strength of the magnetic field. Field discrimination module 120 also receives signals from field direction sensors 58 and determines the directionality of the magnetic field at the respective locations of field direction sensors 58. As described in detail herein, field discrimination module 120 may identify the source of the detected magnetic field as either the primary magnet of MRI device or telemetry head magnet 46 based on the strength and/or the directionality determined using the signals received from field direction sensors 58 and field strength sensor 60. Subsequently, field discrimination module 120 may indicate the source of the detected magnetic field to processing module 110. In examples where no magnetic field is sensed by field strength sensor 60, field discrimination module 120 may indicate to processing module 110 that no magnetic field is sensed.

Processing module 110 may transition IMD 26 from operation in the normal mode to operation in one of the telemetry head mode or the MRI mode, depending on the source of the magnetic field indicated by field discrimination module 120. Processing module 110 may operate in the normal mode while no magnetic field is detected. While operating in the normal mode, processing module 110 may provide typical sensing, pacing, and defibrillation functions without preparing for communication with telemetry head 24 or preparing IMD 26 for entry into an MRI environment. Operation of processing module 110, however, may change when transitioning IMD 26 from operation in the normal mode to operation in either the telemetry head mode or the MRI mode.

Processing module 110 may transition IMD 26 from operation in the normal mode to operation in the telemetry head mode in response to indication from field discrimination module 120 that the source of the magnetic field is telemetry head magnet 46. While in the telemetry head mode, processing module 110 may control communication module 118 to communicate with telemetry head, e.g., download data from telemetry head 122 and upload data to telemetry head 122.

Processing module 110 may transition IMD 26 from operation in the normal mode to operation in the MRI mode in response to indication from field discrimination module 120 that the source of the magnetic field is the primary magnet of MRI device. While in the MRI mode, processing module 110 may execute commands that prepare IMD 26 for exposure to an MRI environment. For example, processing module 110 may notify an operator, via communication module 118, that the MRI field has been detected and that IMD 26 is configured for operation during an MRI scan. In other examples, processing module 110 may disable telemetry functionality during operation in the MRI mode. With respect to pacing functionality, processing module 110 may control therapy module 114 to operate in an asynchronous mode in which pacing may be provided according to a set timing, i.e., fixed, predetermined timing, and may not be responsive to events sensed by sensing module 116 such as sensed cardiac P or R waves. In other examples, processing module 110 may control IMD 26 to operate in a sensing only mode in which no pacing therapy is provided. When therapy module 114 includes defibrillator functionality, processing module 110 may disable tachycardia detection and defibrillation in the MRI mode so that any electrical noise induced in leads 28 or 30 may not be misinterpreted as a tachycardia event. Processing module 110 may also discontinue storing EGM waveforms in memory 112 and may disable diagnostic functions since the gradient and RF fields may corrupt the EGM waveforms. In some examples, processing module 110 may use other sensors (e.g., a pressure or acceleration sensor), different sense circuitry, or different sense algorithms to detect cardiac activity of the patient. In other examples, processing module 110 may instruct sensing module 116 to filter out signals induced by the MRI fields. It is contemplated that processing module 110 may control sensing module 116 and therapy module 114 according to additional settings not described herein in order to ensure proper operation of IMD 26 during an MRI scan.

Field discrimination module 120 may include programmable settings that are used to identify a detected magnetic field. As described above, the settings may include a lower threshold, an upper threshold, and a magnetic field divergence threshold. In some examples, a user may program the lower threshold, the upper threshold, and the magnetic field divergence threshold. In these examples, the user may enter the lower, upper, and magnetic field divergence thresholds into programmer 22 which may then transfer the lower, upper, and magnetic field divergence thresholds to processing module 110 via communication module 118. Subsequently, processing module 110 may transfer the lower, upper, and magnetic field divergence thresholds to field discrimination module 120 for use by field discrimination module 120 in identifying the detected magnetic field. Additionally, in some examples, the user may query the current lower, upper, and magnetic field divergence thresholds using programmer 22.

In some examples, field discrimination module 120 may include settings for enabling portions the field discrimination functionality. For example, field discrimination module 120 may enable field direction sensors 58, e.g., provide power to field direction sensors 58, in response to detecting a magnetic field with a strength that exceeds a particular threshold, such as the lower threshold. In this manner, when no magnetic field that exceeds the lower threshold is detected, no power is provided to field direction sensors 58, thereby conserving power resources of IMD 26. When a magnetic field that exceeds the lower threshold is detected, field direction sensors 58 may be powered up to measure the divergence in the directionality of the magnetic field. In other instances, field direction sensors 58 may be enabled (powered up) in response to detecting that the magnetic field strength is in the overlapping region. In this manner, field direction sensors 58 remain powered down when field discrimination module 120 is capable of identifying the source of the magnetic field based on strength alone.

In some examples, processing module 110 may be configured to indicate, via communication module 118, to an external computing device when the static MRI field is detected. For example, an external computing device may include programmer 22, or any other computing device within the imaging room in which the MRI device is located. Upon detection of the static MRI field, processing module 110 may indicate, via communication module 118, to the external computing device that the patient has an IMD that is capable of detecting the static MRI field and/or that the static MRI field is detected. The external computing device may then display an indicator to a clinician, e.g., on a display, that IMD 26 has detected the MRI device and is prepared for the MRI scan.

As a further example, upon detection of the static MRI field, processing module 110 may indicate, via communication module 118, to the external computing device that the static MRI field is detected. The external computing device may then send an acknowledgement to IMD 26 in response to the indication received from communication module 118. In response to receipt of the acknowledgement, processor 110 may operate IMD 26 in the MRI mode.

Various examples have been described. These and other examples are within the scope of the following claims.

The invention claimed is:

1. A device comprising:
a housing configured to be implanted in a patient;
a first magnetic field direction sensor located at a first location within the housing and configured to generate a signal representative of a first direction of a magnetic field at the first location;
a second magnetic field direction sensor located at a second location within the housing and configured to generate a signal representative of a second direction of the magnetic field at the second location;
a magnetic field strength sensor configured to generate a signal representative of a strength of the magnetic field; and
a processor configured to identify a source of the magnetic field as being a magnetic resonance imaging (MRI) device based on the signal representative of the strength of the magnetic field and a difference between the signal representative of the first direction of the magnetic field at the first location and the signal representative of the second direction of the magnetic field at the second location,
wherein the processor is configured to operate in an MRI mode in response to identifying the source of the magnetic field as the MRI device.

2. The device of claim 1, wherein the processor is configured to:
compare the strength of the magnetic field to a strength threshold;
operate in a magnet mode in response to the magnitude of the magnetic field exceeding the strength threshold;
compare the absolute difference between the first direction and the second direction to a divergence threshold; and
transition to the MRI mode when the absolute difference between the first direction and the second direction is less than the divergence threshold.

3. The device of claim 1,
further comprising a third magnetic field direction sensor located at a third location within the housing and configured to generate a signal representative of a third direction of the magnetic field at the third location,
wherein the processor is configured to:
determine a first absolute difference between the first and second directions;
determine a second absolute difference between the first and third directions;
determine a third absolute difference between the second and third directions;
compare each of the absolute differences to a divergence threshold;
identify the source of the magnetic field as a handheld magnetic device when any of the absolute differences are greater than or equal to the divergence threshold; and
identify the source of the magnetic field as the MRI device when none of the absolute differences are greater than or equal to the divergence threshold and the strength of the magnetic field is greater than a strength threshold.

4. The device of claim 1, wherein the first and second magnetic field direction sensors generate a signal representative of an angle of the magnetic field relative to a fixed direction.

5. The device of claim 1, wherein the processor is configured to determine an absolute difference between the first direction and the second direction and identify the source of the magnetic field as being the MRI device based on at least the absolute difference between the first direction and the second direction.

6. The device of claim 5, wherein the processor is configured to:
determine a strength of the magnetic field based on the signal generated by the magnetic field strength sensor;
compare the strength of the magnetic field to a strength threshold;
compare the absolute difference between the first direction and the second direction to a divergence threshold;
identify the source of the magnetic field as the MRI device when the strength of the magnetic field is greater than the strength threshold and the absolute difference between the first direction and the second direction is less than the divergence threshold.

7. The device of claim 6, wherein the processor is configured to power up the first and second magnetic field direction sensors in response to the strength of the magnetic field exceeding the strength threshold.

8. The device of claim 6, wherein the processor is configured to identify the source of the magnetic field as a handheld magnetic device when the strength of the magnetic field is greater than the strength threshold and the absolute difference between the first direction and the second direction is greater than or equal to the divergence threshold.

9. The device of claim 8, wherein the processor is configured to operate in a telemetry head mode in response to identifying the source of the magnetic field as the handheld magnetic device.

10. The device of claim 1, wherein the processor is configured to:
determine a strength of the magnetic field based on the signal generated by the magnetic field strength sensor;
compare the strength of the magnetic field to an upper strength threshold; and
identify the source of the magnetic field as the MRI device when the strength of the magnetic field is greater than the upper strength threshold.

11. The device of claim 10, wherein the upper threshold value is greater than 100 milli-Tesla (mT).

12. The device of claim 10, wherein the processor is configured to:
determine an absolute difference between the first and second directions when the strength of the magnetic field is not greater than the upper strength threshold;
compare the absolute difference to a divergence threshold;
identify the source of the magnetic field as the MRI device when the absolute difference is less than the divergence threshold; and
identify the source of the magnetic field as a handheld magnetic device when the absolute difference is greater than or equal to the divergence threshold.

13. The device of claim 10, wherein the processor is configured to:
provide power to the magnetic field strength sensor and inhibit power delivery to the first and second magnetic field direction sensors when the strength of the magnetic field is less than a lower strength threshold; and
provide power to the first and second magnetic field direction sensors when the strength of the magnetic field is greater than the lower strength threshold.

14. The device of claim 10, wherein the processor is configured to:
provide power to the magnetic field strength sensor and inhibit power delivery to the first and second magnetic field direction sensors when the strength of the magnetic field is less than a lower strength threshold; and
provide power to the first and second magnetic field direction sensors when the strength of the magnetic field is greater than the lower strength threshold and less than the upper strength threshold.

15. A method comprising:
obtaining a signal representative of a first direction of a magnetic field at a first location within an implantable medical system;
obtaining a signal representative of a second direction of a magnetic field at a second location within the implantable medical system;
obtaining a signal representative of a strength of the magnetic field;
identifying a source of the magnetic field as being a magnetic resonance imaging (MRI) device based on the signal representative of the strength of the magnetic field and a difference between the signal representative of the first direction of the magnetic field at the first location and the signal representative of the second direction of the magnetic field at the second location; and
transitioning operation of the implantable medical system to an MRI mode in response to identifying the source of the magnetic field as the MRI device.

16. The method of claim 15, further comprising selectively providing power to the first and second magnetic field direction sensors based on the signal generated by the magnetic field strength sensor such that power delivery is inhibited to the first and second magnetic field direction sensors when a strength of the magnetic field is less than a strength threshold and power is delivered to the first and second magnetic field direction sensors when the strength of the magnetic field is greater than the strength threshold.

17. The method of claim 15, further comprising:
obtaining a signal representative of a third direction of the magnetic field at the third location within the implantable medical system;
wherein identifying a source of the magnetic field comprises:
comparing a strength of the magnetic field to a strength threshold;
determining a first absolute difference between the first and second directions;
determining a second absolute difference between the first and third directions;
determining a third absolute difference between the second and third directions;
comparing each of the absolute differences to a divergence threshold;
identifying the source of the magnetic field as a handheld magnetic device when a strength of the magnetic field exceeds a strength threshold and any of the absolute differences is greater than or equal to the divergence threshold; and
identifying the source of the magnetic field as the MRI device when the strength of the magnetic field exceeds the strength threshold and none of the absolute differences are greater than or equal to the divergence threshold.

18. The method of claim 15, wherein identifying a source of the magnetic field comprises:
determining an absolute difference between the first direction and the second direction;
determining a strength of the magnetic field;
comparing the strength of the magnetic field to a strength threshold;
comparing the absolute difference between the first direction and the second direction to a divergence threshold;
identifying the source of the magnetic field as the MRI device when the strength of the magnetic field is greater than the strength threshold and the absolute difference between the first direction and the second direction is less than the divergence threshold; and
identifying the source of the magnetic field as a handheld magnetic device when the strength of the magnetic field is greater than the strength threshold and the absolute difference between the first direction and the second direction is greater than or equal to the divergence threshold.

19. The method of claim 18, further comprising:
operating the implantable medical system in a telemetry head mode in response to identifying the source of the magnetic field as the handheld magnetic device.

20. The method of claim 15, wherein identifying a source of the magnetic field comprises:
determining a strength of the magnetic field based on the signal generated by the magnetic field strength sensor;
comparing the strength of the magnetic field to an upper strength threshold; and
identifying the source of the magnetic field as the MRI device when the strength of the magnetic field is greater than or equal to the upper strength threshold.

21. The method of claim 20, wherein identifying a source of the magnetic field comprises:
comparing the strength of the magnetic field to a lower strength threshold;
determining an absolute difference between the first and second directions when the strength of the magnetic field is greater than or equal to the lower strength threshold and less than the upper strength threshold;
comparing the absolute difference to a divergence threshold;
identifying the source of the magnetic field as the MRI device when the absolute difference is less than the divergence threshold; and
identifying the source of the magnetic field as a handheld magnetic device when the absolute difference is greater than or equal to the divergence threshold.

22. A non-transitory computer-readable storage medium comprising instructions that, when executed, cause a programmable processor to:
obtain a signal representative of a first direction of a magnetic field at a first location within an implantable medical system;
obtain a signal representative of a second direction of a magnetic field at a second location within the implantable medical system;
obtain a signal representative of a strength of the magnetic field;
identify a source of the magnetic field as being a magnetic resonance imaging (MRI) device based on the signal representative of the strength of the magnetic field and a difference between the signal representative of the first direction of the magnetic field at the first location and the signal representative of the second direction of the magnetic field at the second location; and operate the implantable medical system in a MRI mode in response to identifying the source of the magnetic field as the MRI device.

23. The computer-readable storage medium of claim 22, further comprising instructions that, when executed, cause the programmable processor to selectively provide power to the first and second magnetic field direction sensors based on the signal generated by the magnetic field strength sensor such that power delivery is inhibited to the first and second magnetic field direction sensors when a strength of the magnetic field is less than a strength threshold and power is delivered to the first and second magnetic field sensors when the strength of the magnetic field is greater than the strength threshold.

24. The computer-readable storage medium of claim 22, wherein the instructions that cause the programmable processor to identify a source of the magnetic field comprise instructions to:

determine a strength of the magnetic field based on the signal generated by the magnetic field strength sensor;

compare the strength of the magnetic field to a lower strength threshold and an upper strength threshold;

identify the source of the magnetic field as the MRI device when the strength of the magnetic field is greater than or equal to the upper strength threshold;

determine an absolute difference between the first and second directions when the strength of the magnetic field is greater than or equal to the lower strength threshold and less than the upper strength threshold;

compare the absolute difference to a divergence threshold;

identify the source of the magnetic field as the primary magnet of the MRI device when the absolute difference is less than the divergence threshold; and identify the source of the magnetic field as a handheld magnetic device when the absolute difference is greater than or equal to the divergence threshold.

25. The computer-readable storage medium of claim 22, further comprising instructions that, when executed, cause the processor to obtain a signal representative of a third direction of the magnetic field at the third location within the implantable medical system, wherein instruction to identify the source of the magnetic field comprise instructions that, when executed cause the processor to:

compare a strength of the magnetic field to a strength threshold;

determine a first absolute difference between the first and second directions;

determine a second absolute difference between the first and third directions;

determine a third absolute difference between the second and third directions;

compare each of the absolute differences to a divergence threshold;

identify the source of the magnetic field as a handheld magnetic device when a strength of the magnetic field exceeds a strength threshold and any of the absolute differences is greater than or equal to the divergence threshold; and identify the source of the magnetic field as the MRI device when the strength of the magnetic field exceeds the strength threshold and none of the absolute differences are greater than or equal to the divergence threshold.

26. The computer-readable storage medium of claim 22, wherein the instructions that cause the programmable processor to identify a source of the magnetic field comprise instructions to:

determine an absolute difference between the first direction and the second direction;

determine a strength of the magnetic field;

compare the strength of the magnetic field to a strength threshold;

compare the absolute difference between the first direction and the second direction to a divergence threshold;

identify the source of the magnetic field as the MRI device when the strength of the magnetic field is greater than the strength threshold and the absolute difference between the first direction and the second direction is less than the divergence threshold; and identify the source of the magnetic field as a handheld magnetic device when the strength of the magnetic field is greater than the strength threshold and the absolute difference between the first direction and the second direction is greater than or equal to the divergence threshold.

27. The computer-readable storage medium of claim 26, further comprising instruction that, when executed, cause the processor to:

operate the implantable medical system in a telemetry head mode in response to identifying the source of the magnetic field as the handheld magnetic device.

* * * * *